United States Patent [19]

Renfroe

[11] Patent Number: 4,478,842

[45] Date of Patent: Oct. 23, 1984

[54] N-SUBSTITUTED-2-PYRIDYLINDOLES

[75] Inventor: Harris B. Renfroe, West Nyack, N.Y.

[73] Assignee: Ciba-Geigy Corporation, Ardsley, N.Y.

[21] Appl. No.: 437,420

[22] Filed: Nov. 1, 1982

Related U.S. Application Data

[63] Continuation-in-part of Ser. No. 323,018, Nov. 19, 1981, abandoned.

[51] Int. Cl.$^3$ .................... A61K 31/44; C07D 401/04; C07D 413/14
[52] U.S. Cl. .................................. 424/263; 546/270; 546/273
[58] Field of Search ................. 546/273, 270; 424/263

[56] References Cited

U.S. PATENT DOCUMENTS

| | | | |
|---|---|---|---|
| 3,182,071 | 5/1965 | Shavel | 260/245.7 |
| 3,285,908 | 11/1966 | Shen | 536/53 |
| 3,454,586 | 7/1969 | Suh | 546/273 |
| 3,467,670 | 9/1969 | Suh | 548/506 |
| 3,468,894 | 9/1969 | Pfenninger | 424/263 |
| 3,491,111 | 1/1970 | Suh | 260/326 |
| 3,491,114 | 1/1970 | Suh | 548/505 |
| 3,557,142 | 1/1971 | Bell | 548/516 |
| 3,856,967 | 1/1924 | Allais et al. | 424/274 |
| 4,273,782 | 6/1981 | Cross et al. | 424/273 R |
| 4,343,811 | 9/1982 | Hurnaus | 424/274 |
| 4,363,912 | 12/1982 | Cross et al. | 424/263 |

FOREIGN PATENT DOCUMENTS 54417 6/1982 European Pat. Off. .
42-17904 9/1967 Japan .

OTHER PUBLICATIONS

Kahnt et al., Acta. Endocrinologica, 70 (1972), 315–330.
Buchmann, Pharmazie 23, 557–560 (1968).
Sugasawa et al., Pharm. Bull. Japan 4, 16–19 (1956).
Buchamann et al., CA. 64, 19540d (1966).
Fetzion et al., Bull. Soc. Chim., France 1969, 4154–4159.
Takahashi et al., Chem. Abstracts, 1964, 1694d.
Fetizon et al., Bull. Soc. Chim., France 1966, 771–772.

*Primary Examiner*—Jane T. Fan
*Attorney, Agent, or Firm*—Norbert Gruenfeld

[57] ABSTRACT

Various 1-carboxylic acid substituted-2-pyridylindoles and functional derivatives thereof are highly specific thromboxane synthetase inhibitors. Synthesis of, pharmaceutical compositions thereof, and methods of treatment utilizing such compounds are included.

22 Claims, No Drawings

N-SUBSTITUTED-2-PYRIDYLINDOLES

CROSS-REFERENCE TO RELATED APPLICATIONS

This is a continuation-in-part of application Ser. No. 323,018 filed Nov. 19, 1981, now abandoned.

BACKGROUND OF THE INVENTION

U.S. Pat. No. 3,468,894 disclosed the 1-unsubstituted 3-methyl-2-(3- or 4-pyridyl)indoles as diuretic agents. 2-(2-Pyridyl)indole-3-(acetic, propionic) acids are reported e.g., in Pharm. Bull. 4, 16 (1956) and Chemical Abstracts 64, 19540d (1966) respectively. Various optionally substituted 2-(3-pyridyl)-indole-3-acetic acids have been described as chemical intermediates in Bull. Soc. Chim. France 1966, 771-2 and Bull. Soc. Chim. France 1969, 4154-9. The preparation of 1-cyanoethyl-2-(2-pyridyl)-indole is reported in Pharmazie 23 (10), 557-60 (1968).

Reported as thromboxane synthetase inhibitors are e.g., 3-(imidazol-1-yl-alkyl)indoles of U.S. Pat. No. 4,217,357 and 4,273,782 and 1-substituted imidazoles of U.S. Pat. No. 4,256,757 and British patent application No. 2,016,452A.

The present invention is concerned with N-(or 1)-substituted-2-pyridylindoles of formula I representing a novel class of pharmaceuticals. For example, the compounds of formula I are surprisingly potent and highly specific thromboxane synthetase inhibitors.

The foregoing attributes render the N-substituted-2-pyridyl indoles of this invention particularly useful when administered, alone or in combination, to mammals, e.g. for the treatment or prevention of diseases responsive to the inhibition of thromboxane synthetase, comprising cardiovascular disorders such as thrombosis, atherosclerosis, coronary spasm, arrhythmias, cerebral ischaemic attacks, migraine and other vascular headaches, myocardial infarction, angina pectoris, hypertension; respiratory disorders, such as asthma and apnea; and inflammatory disorders. Inhibition of thromboxane synthetase also has been noted to decrease metastasis in certain classes of tumors, and the compounds of this invention may thus be useful for the treatment of certain carcinomas.

SUMMARY OF THE INVENTION

This invention relates to N(or 1)-substituted-2-pyridylindoles of formula I which are useful as selective thromboxane synthetase inhibitors, processes for preparing same, pharmaceutical compositions comprising said compounds, and methods of treating syndromes, conditions and diseases in mammals responsive to the inhibition of thromboxane synthetase by administration of said compounds and compositions.

Particularly the invention relates to the 1-substituted 2-pyridylindoles of formula I

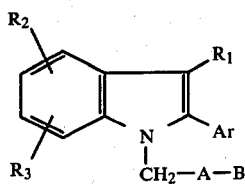

(I)

wherein $R_1$ represents hydrogen or lower alkyl;
Ar represents pyridyl unsubstituted or substituted by lower alkyl, carboxy, lower alkoxycarbonyl or carbamoyl;
$R_2$ and $R_3$ independently represent hydrogen, lower alkyl, halogen, trifluoromethyl, hydroxy, lower alkoxy, carboxy lower alkyl, lower alkoxycarbonyl lower alkyl, carboxy, lower alkoxycarbonyl, or lower alkyl-(thio, sulfinyl or sulfonyl), or $R_2$ and $R_3$ together on adjacent carbon atoms represent lower alkylenedioxy;
A represents straight chain or branched alkylene of 1 to 12 carbon atoms, alkenylene of 2 to 12 carbon atoms, alkynylene of 2 to 12 carbon atoms, lower alkylenephenylene lower alkylene, lower alkylenephenylene, phenylene lower alkylene, phenylene, a direct bond, lower alkylene-(thio or oxy)-lower alkylene, (thio- or oxy)-phenylene, lower alkylene-(thio or oxy)-phenylene, phenylene-(thio or oxy)-lower alkylene or phenylene lower alkenylene;
B represents carboxy, lower alkoxycarbonyl, carbamoyl, mono- or di-lower alkylcarbamoyl, hydroxymethyl, hydroxycarbamoyl, 5-tetrazolyl or formyl; the N-oxides thereof; and pharmaceutically acceptable salts thereof.

DETAILED DESCRIPTION OF THE INVENTION

Preferred embodiments of this invention relate to compounds of formula I wherein $R_1$ represents hydrogen or lower alkyl;
Ar represents 2-, 3- or 4-pyridyl or 2-, 3- or 4-pyridyl substituted by lower alkyl;
$R_2$ is hydrogen, lower alkyl, halogen, trifluoromethyl, hydroxy, lower alkoxy, lower alkylthio, carboxy lower alkyl or lower alkoxycarbonyl lower alkyl;
$R_3$ is hydrogen; or $R_2$ and $R_3$ together on adjacent carbon atoms represent lower alkylenedioxy;
A represents straight chain or branched alkylene of 1 to 12 carbon atoms, phenylene, lower(alkylenephenylene, alkylene-thio-phenylene or alkylene-oxy-phenylene) of 7 to 10 carbon atoms, or a direct bond;
B represents carboxy, lower alkoxycarbonyl, carbamoyl, hydroxycarbamoyl, 5-tetrazolyl, or hydroxymethyl; thereof; and pharmaceutically acceptable salts thereof.

Further preferred are said compounds of formula I wherein $R_2$ is attached at the 5-position of the indole nucleus.

Particularly preferred are said compounds of formula I wherein B represents carboxy, lower alkoxycarbonyl, carbamoyl, 5-tetrazolyl or hydroxycarbamoyl.

Greatly preferred are the compounds of formula I wherein A represents straight chain or branched alkylene of 3 to 10 carbon atoms, phenylene, lower alkylene-thio-phenylene or lower alkylene-oxy-phenylene of 7 to 10 carbon atoms each.

Very useful are the compounds of formula I wherein A represents straight chain or branched alkylene of 1 to 12 carbon atoms, a direct bond or phenylene.

Particularly useful are compounds of formula II

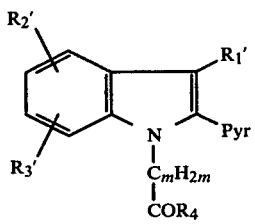

(II)

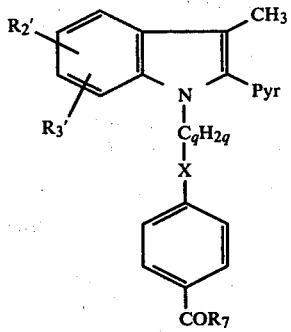

(IV)

wherein $R_1'$ represents hydrogen or lower alkyl;

$R_2'$ and $R_3'$ represent independently hydrogen, lower alkyl, halogen, trifluoromethyl, hydroxy, lower alkylthio or lower alkoxy; or $R_2'$ and $R_3'$ together on adjacent carbon atoms represent methylenedioxy;

Pyr represents 2-, 3- or 4-pyridyl;

m represents an integer from 1 to 13;

$R_4$ represents hydroxy, lower alkoxy or amino; and pharmaceutically acceptable salts thereof.

Preferred are the compounds of formula II wherein $R_3'$ represents hydrogen.

Especially valuable are compounds of formula II wherein $R_1'$ represents methyl, ethyl, propyl;

$R_2'$ represents hydrogen, methyl, chloro, fluoro, trifluoromethyl, hydroxy, methylthio or methoxy; $R_3'$ represents hydrogen;

m represents an integer from 3 to 10;

$R_4$ represents hydroxy, ethoxy, methoxy or amino;

Pyr represents 3- or 4-pyridyl; and pharmaceutically acceptable salts thereof.

Most preferred are the compounds of formula II wherein $R_1'$ represents methyl; $R_2'$ represents hydrogen or chloro; $R_3'$ represents hydrogen; m is 4 to 8; Pyr represents 3- or 4-pyridyl, and $R_4$ represents hydroxy, ethoxy, methoxy or amino. Particularly useful are also compounds of formula III

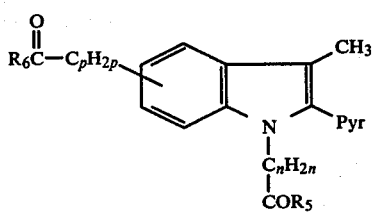

(III)

wherein n represents an integer from 3 to 10;

p represents an integer from 0 to 4;

Pyr represents 2-, 3- or 4-pyridyl;

$R_5$ and $R_6$ independently represent hydroxy or lower alkoxy; and pharmaceutically acceptable salts thereof.

Preferred are compounds of formula III wherein n is 4 to 8, p is 1 to 4; Pyr is 3- or 4-pyridyl; $R_5$ and $R_6$ represent hydroxy.

Also valuable are compounds of formula IV wherein $R_2'$ and $R_3'$ independently represent hydrogen, lower alkyl, halogen, lower alkoxy, lower alkylthio or hydroxy; or $R_2'$ and $R_3'$ together on adjacent carbon atoms represent methylenedioxy; X represents oxygen, sulfur or a direct bond; q represents an integer from 1 to 4; $R_7$ represents hydroxy or lower alkoxy; Pyr represents 2-, 3- or 4-pyridyl, and pharmaceutically acceptable salts thereof.

Preferred are the compounds of formula IV wherein X is a direct bond. Also preferred are the compounds of formula IV wherein q is an integer from 2 to 4 and X is oxygen or sulfur.

Further preferred are compounds of formula IV wherein $R_2'$ represents hydrogen, methyl, chloro, fluoro, trifluoromethyl, hydroxy, methylthio or methoxy; $R_3'$ represents hydrogen; q represents an integer from 1 to 4; $R_7$ represents hydroxy or lower alkoxy; Pyr represents 2-, 3- or 4-pyridyl; and pharmaceutically acceptable salts thereof.

Particularly preferred are compounds of formula IV wherein $R_2'$=H; q=1; X=a direct bond; Pyr=3- or 4-pyridyl; and $R_7$=hydroxy.

The general definitions used herein have the following meanings within the scope of the present invention.

A straight chain or branched alkylene represents $C_{1-12}$ alkylene preferably propylene, butylene, pentylene, hexylene, or heptylene, said radicals being unsubstituted or substituted by one or more lower alkyl groups with the proviso that the total number of carbon atoms equals no more than 12.

The term "straight chain or branched alkenylene" represents $C_{2-12}$ alkenylene groups preferably propenylene, 1- or 2-butenylene, 1- or 2-pentenylene, 1-, 2- or 3-hexenylene, 1-,2-,3 or 4-heptenylene, said groups being unsubstituted or substituted by one or more lower alkyl groups with the proviso that the total number of carbon atoms equals no more than 12.

The term "straight chain or branched alkynylene" represents $C_2$–$C_{12}$ alkynylene preferably propynylene, 1- or 2-butynylene, 1-or 2-pentynylene, 1-, 2- or 3-hexynylene, 1-, 2-, 3- or 4-heptynylene, said radicals being unsubstituted or substituted by one or more lower alkyl groups with the proviso that the total number of carbon atoms equals no more than 12. The term phenylene represents 1,2-, 1,3- and preferably 1,4-phenylene. The term pyridyl represents 2-, 3- and 4-pyridyl, preferably 3-pyridyl.

The term "lower" when referred to above and hereinafter in connection with organic groups, radicals or compounds respectively defines such with up to and including 7, preferably up to and including 4 and advantageously one, two or three carbon atoms.

A lower alkylenephenylene group, a phenylene lower alkylene group, a lower alkylenephenylene lower alkylene group, a lower alkylene-(thio or oxy)-phenylene group, a phenylene-(thio or oxy)-lower alkylene group, or a phenylene lower alkenylene group preferably contains 1 to 4 carbon atoms and advantageously one or two carbon atoms in each alkylene or alkenylene portion. The lower alkylene and alkenylene portions may be straight chain or branched.

A lower alkylene-(thio or oxy)-lower alkylene group is straight chain or branched and may contain a total of 2 to 12 carbon atoms, preferably 2 to 8 carbon atoms.

A lower alkyl group preferably contains 1–4 carbon atoms and represents for example ethyl, propyl, butyl or advantageously methyl.

A lower alkylenedioxy group represents preferably ethylene-dioxy and methylene-dioxy.

A lower alkoxy group preferably contains 1–4 carbon atoms and represents for example, ethoxy, propoxy or advantageously methoxy. A lower alkyl-(thio, sulfinyl or sulfonyl) group represents advantageously methylthio, methylsulfinyl or or methylsulfonyl respectively.

A lower alkoxycarbonyl group preferably contains 1–4 carbon atoms in the alkoxy portion and represents for example: methoxycarbonyl, propoxycarbonyl, isopropoxycarbonyl or advantageously ethoxycarbonyl. A mono(lower alkyl)-carbamoyl group preferably contains 1–4 carbon atoms in the alkyl portion and is for example N-methylcarbamoyl, N-propylcarbamoyl, or advantageously N-ethylcarbamoyl. A di(lower alkyl)-carbamoyl group preferably contains 1–4 carbon atoms in each lower alkyl portion and represents for example N,N-dimethylcarbamoyl, N-methyl-N-ethylcarbamoyl and advantageously N,N-diethylcarbamoyl.

Halogen is preferably fluorine and chlorine, but may also represent bromine or iodine.

Pharmaceutically acceptable salts are preferably metal or ammonium salts or said compounds of formula I having a free carboxy group, more particularly alkali or alkaline earth metal salts, e.g., the sodium, potassium, magnesium or calcium salt; or advantageously easily crystallizing ammonium salts derived from ammonia or organic amines, such as mono-, di- or tri-lower (alkyl, cycloalkyl or hydroxyalkyl)-amines, lower alkylenediamines or lower (hydroxyalkyl or aralkyl)-alkylammonium hydroxides, e.g., methylamine, diethylamine, triethylamine, dicyclohexylamine, triethanolamine, ethylenediamine, tris-(hydroxymethyl)aminomethane or benzyltrimethylammonium hydroxide. Said compounds of Formula I form acid addition salts of preferably the pharmaceutically acceptable inorganic or organic acids, such as of strong mineral acids, for example hydrohalic; e.g. hydrochloric or hydrobromic acid; sulfuric, phosphoric, nitric or perchloric acid; aliphatic or aromatic carboxylic or sulfonic acids, e.g. formic, acetic, propionic, succinic, glycolic, lactic, malic, tartaric, gluconic, citric, ascorbic, maleic, fumaric, pyruvic, phenylacetic, benzoic, 4-aminobenzoic, anthranilic, 4-hydroxybenzoic, salicylic, 4-aminosalicylic, pamoic, nicotinic, methanesulfonic, ethanesulfonic, hydroxyethanesulfonic, benzenesulfonic, p-toluenesulfonic, naphthalenesulfonic, sulfanilic or cyclohexylsulfamic acid.

The compounds of this invention exhibit valuable pharmacological properties, e.g. cardiovascular effects, by selectively decreasing thromboxane levels through selective inhibition of thromboxane synthetase in mammals. The compounds are thus useful for treating diseases responsive to thromboxane synthetase inhibition in mammals, primarily cardiovascular disorders such as thrombosis, atherosclerosis, coronary spasm, cerebral ischaemic attacks, migraine and other vascular headaches, myocardial infarction, angina pectoris, and hypertension.

These effects are demonstrable in in vitro tests or in vivo animal tests using advantageously mammals, e.g. guinea pigs, mice, rats, cats, dogs, or monkeys. Said compounds can be administered to them enterally or parenterally, advantageously orally, or subcutaneously, intravenously or intraperitoneally, for example, within gelatin capsules, or in the form of starchy suspensions or aqueous solutions respectively. The applied dosage may range between about 0.01 to 100 mg/kg/day, preferably between about 0.05 and 50 mg/kg/day, advantageously between about 0.1 and 25 mg/kg/day.

The in vitro inhibition of the thromboxane synthetase enzyme can be demonstrated, analogous to the method of Sun, Biochem. Biophys. Res. Comm. 74, 1432 (1977); the testing procedure is as follows:

$^{14}C$-Arachidonic acid is incubated with an enzyme consisting of solubilized and partially purified prostaglandin cyclo-oxygenase from sheep seminal vesicles and a crude microsomal preparation of thromboxane synthetase from lysed human platelets. The test compound (dissolved in buffer, or if necessary, in a small amount of ethanol) is added to the incubation medium. At the end of the incubation period (30 minutes), Prostaglandin E2 (PGE$_2$) is reduced to a mixture of Prostaglandin F$_2\alpha$ and F$_2\beta$ (PGF$_2\alpha+\beta$) by addition of sodium borohydride. The radioactive products and excess substrate are extracted into ethyl acetate; the extract is evaporated to dryness; the residue is dissolved in acetone, spotted on thin-layer plates and chromatographed in the solvent system toluene: acetone: glacial acetic acid (100 volumes: 100 volumes: 3 volumes). The radioactive zones are located; those corresponding to Thromboxane B$_2$ (TxB$_2$) and PGF$_2\alpha+\beta$ are transferred to liquid scintillation vials and counted. The ratio of counts for TxB$_2$/PGF$_2\alpha+\beta$ is calculated for each concentration of test compound and IC$_{50}$ values are determined graphically as the concentration of test compound at which the ratio of TxB$_2$/PGF$_2\alpha+\beta$ is reduced to 50% of the control value.

The in-vitro effect on prostaglandin cyclooxygenase is measured by a modification of the method of Takeguchi et al. described in Biochemistry 10, 2372 (1971); the testing procedure is as follows:

Lyophilized sheep seminal vesicle microsomes are utilized as the prostaglandin-synthesizing enzyme preparation. The conversion of $^{14}C$-arachidonic acid to PGE2 is measured. Test compounds (dissolved in buffer, or if necessary, in a small amount of ethanol) are added to the incubation mixture. The prostaglandins are extracted and separated by thin-layer chromatography; the plates are scanned, the radioactive zones corresponding to PGE$_2$ are transferred to liquid scintillation vials and counted for radioactivity. IC$_{50}$ values for inhibition are determined graphically as the concentration of test compound causing a 50% reduction in the amount of PGE$_2$ synthesized.

The in-vitro effect on prostacyclin (PGI$_2$) synthetase is measured analogous to the method of Sun et al., Prostaglandins 14, 1055 (1977);

The testing procedure is as follows:

$^{14}C$-Arachidonic acid is incubated with an enzyme mixture consisting of solubilized and partially purified prostaglandin cyclo-oxygenase from sheep seminal vesicles and crude PGI$_2$ synthetase in the form of a microsomal fraction of bovine aorta.

Test compound (dissolved in buffer, or if necessary, in a small amount of ethanol) is placed in the incubation medium. The reaction mixture is incubated in 100 mM Tris HCl (pH 7.5) for 30 minutes at 37° C., acidified to pH 3 and extracted into ethyl acetate. The extract is evaporated to dryness; the residue is dissolved in acetone, spotted on thin-layer plates and chromatographed in a solvent system described by Sun et al. The radioactive zones are located with a scanner; those corresponding to 6-keto-PGF$_{1\alpha}$(a stable end product of prostacyclin biotransformation) and PGE$_2$ are transferred to liquid scintillation vials and counted. The ratio of counts for 6-keto-PGF$_{1\alpha}$/PGE$_2$ is calculated for each concentration of test compound used. IC$_{50}$ values for inhibition are determined graphically as the concentration of test compound at which the ratio of 6-keto-PGF$_{1\alpha}$/PGE$_2$ is reduced to 50% of the control value.

The inhibition of the synthesis and the reduction of plasma levels of thromboxane is determined in vivo on administration to rats in the following manner (as adapted from the procedures described by Tai et al. in Anal. Biochem. 87:343, 1978 and by Salmon in Prostaglandins 15:383, 1978):

Rats are dosed with vehicle or test drug and injected intravenously with ionophore A23187 (0.5 mg/kg) two hours later. Blood is collected for analysis 2 minutes after the ionophore injection. A single aliquot of each plasma sample is assayed for thromboxane B$_2$ and another aliquot for 6-keto-PGF$_{1\alpha}$, the stable metabolites of thromboxane A$_2$ and prostacyclin (PGI$_2$) respectively, by radioimmunoassay.

Compounds of the formula I are very potent and selective, thromboxane synthetase inhibitors. At and above the effective dose levels for thromboxane synthetase inhibition neither the beneficial prostacyclin synthetase enzyme system nor the prostaglandin cyclooxygenase enzyme system is significantly inhibited. Surprisingly, the prostacyclin levels are significantly increased.

Illustrative of the invention, the IC$_{50}$ for 1-(7-carboxyheptyl)-3-methyl-2-(3-pyridyl)indole of example 1 is $1.2 \times 10^{-8}$M for thromboxane synthetase inhibition whereas the IC$_{50}$ for both inhibition of prostacyclin synthetase and cyclooxygenase is several orders of magnitude higher, i.e. about $1 \times 10^{-4}$M.

Furthermore the IC$_{50}$ for thromboxane synthetase inhibition is e.g. $2 \times 10^{-8}$M for compound of example 9, namely 1-(5-carboxypentyl)-5-(2-carboxyethyl)-3-methyl-2-(3-pyridyl)indole, $5 \times 10^{-8}$M for 1-(4-carboxybenzyl)-3-methyl-2-(3-pyridyl)indole, the compound of example 11, $1 \times 10^{-9}$M for 1-(5-carboxypentyl)-5-chloro-3-methyl-2-(3-pyridyl)indole, the compound of example 7, $1 \times 10^{-8}$M for 1-(5-carbamoylpentyl)-5-chloro-3-methyl-2-(3-pyridyl)indole, the compound of example 13, $2.6 \times 10^{-8}$M for 1-[2-(4-carboxyphenoxy)ethyl]-2-(3-pyridyl)-3-methylindole of Example 20 and $5.8 \times 10^{-8}$M for 1-[2-(4-carboxyphenylthio)ethyl]-2-(3-pyridyl)-3-methylindole hydrochloride of Example 22.

1-(7-Carboxyheptyl-3-methyl-2-(3-pyridyl)indole of example 1 and 1-(5-carboxypentyl)-5-chloro-3-methyl-2-(3-pyridyl)indole of example 7, as representative compounds of the invention, decrease the plasma concentration of thromboxane B$_2$ by over 50% in the rat at an oral dose as low as 0.10 mg/kg; a surprising increase in the plasma level of prostacyclin is observed at this or a higher dose thereof.

The aforementioned advantageous properties render the compounds of this invention of great value as specific therapeutic agents for mammals including man.

Indicative of the utility in thromboembolism, compounds of this invention, e.g. 1-(7-carboxyheptyl)-3-methyl-2-(3-pyridyl) indole of example 1 inhibits variously induced platelet aggregation and thrombocytopenia. Experimentally, prolongation of bleeding time in the rat is indicative of a beneficial antithrombotic effect. The compounds of this invention prolong bleeding time, e.g. 1-(7-carboxyheptyl)-3-methyl-2(3-pyridyl) indole of example 1 prolongs bleeding time when administered orally to rats at a dose of about 30 mg/kg.

Indicative of the beneficial effect in respiratory disorders, the compounds of this invention afford protection against sudden death due to arachidonic acid induced pulmonary obstruction, e.g. 1-(7-carboxyheptyl)-3-methyl-2-(3-pyridyl) indole of example 1 protects against sudden death when administered orally to mice at a dose of 100 mg/kg.

In addition to the pharmaceutically acceptable salts cited above, any prodrug derivatives thereof, e.g., pharmaceutically acceptable esters and amides of the carboxylic acids of this invention that may be convertible by solvolysis or under physiological conditions to the said carboxylic acids, represent a further object of this invention.

Said esters are preferably e.g., the straight chain or branched lower alkyl esters unsubstituted or suitably substituted such as the pivaloyloxymethyl, 2-diethylaminoethyl, bornyloxycarbonylmethyl, α-carboxyethyl or suitably esterified α-carboxyethyl esters and the like which are prepared by methods well known to the art.

Said amides are preferably e.g. simple primary and secondary amides and amides derived from the amino acids or derivatives thereof, such as the amides derived from alanine, phenylalanine and the like.

The compounds of formula I according to the invention can be prepared in a manner which is known per se comprising, e.g.

(1) condensing a compound of the formula V

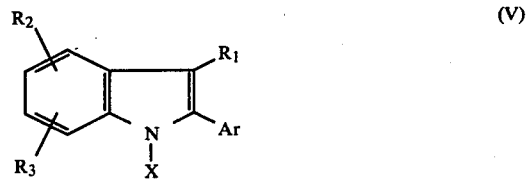

wherein R$_1$, R$_2$, R$_3$ and Ar have meaning as defined above, and X represents hydrogen, alkali metal or tri-(lower)alkylsilyl, with a reactive funtional derivative of a compound of the formula VI

HOCH$_2$—A—B  (VI)

A and B have meaning as defined above, with optional temporary protection of interfering reactive groups;

(2) ring-closing a compound of formula VII

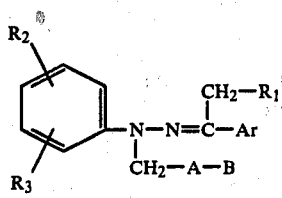

wherein Ar, $R_1$, $R_2$, $R_3$, A and B having meaning as defined above;

(3) cyclizing a compound of the formula VIII

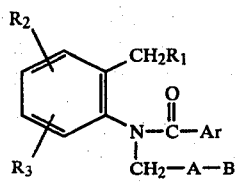

wherein Ar, $R_1$, $R_2$, $R_3$, A and B have meaning as defined above;

(4) converting into a compound of formula I a compound of the formula Ia

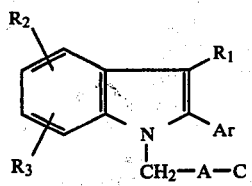

wherein A, Ar, $R_1$, $R_2$ and $R_3$ have meaning as defined above and C is a group differing from B and convertible into B, and/or if desired, converting a resulting compound of formula I into another compound of formula I, and/or if desired converting a resulting compound of formula I into a salt thereof, or liberating a free compound from such salt; and/or if appropriate, isolating an optical or geometric isomer which is enriched from a mixture of isomeric forms of a resulting compound of formula I.

The condensation according to process (1) is preferably carried out under basic conditions, e.g. with a basic alkali metal salt or a quaternary ammonium salt such as tetrabutyl ammonium hydroxide. For example, more specifically the compounds of formula V wherein X is hydrogen are converted preferably in situ, to reactive organometallic intermediates with a reactive metallizing agent, preferably about one molar equivalent of e.g. a strong alkali metal base, such as lithium diisopropylamide, sodium hydride, potassium t-butoxide in an inert solvent such as dimethylformamide or tetrahydrofuran at a temperature range between $-50°$ to $+75°$ preferably between $-25°$ and $+50°$. Condensation of the resulting reactive organometallic compound of formula V with a reactive esterified derivative of a compound of formula VI proceeds at a temperature range from about $-25°$ to $+50°$, preferably at a temperature range of $0°$ to $30°$. In the case where B represents carboxy, carbamoyl, hydroxycarbamoyl, mono lower alkylcarbamoyl, additional, e.g. one molar equivalent of metallizing agent is required.

The intermediates of formula V wherein X is hydrogen are either known to the art (e.g. U.S. Pat. No. 3,468,894; J. Chem. Soc. 1955, 2865; Bull. Soc. Chim. France 1969, 4154) or are prepared analogously from the corresponding optionally substituted phenylhydrazines and ketones of the formula $ArCOCH_2R_1$ in the presence of a condensing agent, e.g. ethanolic HCl or polyphosphoric acid by the well-known Fischer indole synthesis.

The starting materials of formula VI or formula VIa hereinafter are known or if new, are prepared according to conventional methods, e.g. the methods illustrated in U.S. Pat. No. 4,256,757, British patent application No. 2,016,452A or as described in the examples herein.

More specifically, the compounds of formula I are advantageously prepared according to process (1) as follows:

(a) Condensing preferably under basic conditions a compound of the formula V

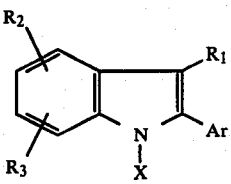

wherein

X is hydrogen;

$R_1$ represents hydrogen or lower alkyl;

Ar represents pyridyl or pyridyl substituted by lower alkyl, carboxy, lower alkoxycarbonyl or carbamoyl;

$R_2$ and $R_3$ represent hydrogen, lower alkyl, halogen, trifluoromethyl, hydroxy, lower alkoxy, carboxy lower alkyl or lower alkoxycarbonyl lower alkyl, carboxy or lower alkoxycarbonyl; with a reactive functional derivative of a compound of the formula VIa

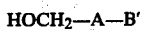

$$HOCH_2-A-B' \quad \text{(VIa)}$$

wherein A represents straight chain or branched alkylene of 1 to 12 carbon atoms, alkenylene of 2 to 12 carbon atoms, alkynylene of 2 to 12 carbon atoms, lower alkylenephenylene lower alkylene, lower alkylenephenylene, phenylene lower alkylene, phenylene or a direct bond; and B' represents carboxy, lower alkoxycarbonyl, carbamoyl, mono- or di-lower alkylcarbamoyl, hydroxymethyl, etherified hydroxymethyl, halomethyl, trialkoxymethyl or cyano; to yield a compound of formula Ib

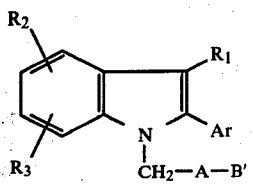

wherein Ar, $R_1$, $R_2$, $R_3$, A and B' have meanings as defined above;

optionally hydrolyzing or derivatizing the resulting product; and converting any resulting compound into another compound of formula I.

The optional steps of hydrolyzing or derivatizing the initial product [part a] of the aforesaid process and the conversion of the resulting product into another compound of this invention are performed by chemical methodology known to the art.

The ring closure according to process (2) of the intermediates of formula VII is carried out by the well-known Fischer indole synthesis [as described in "Heterocyclic Compounds, Indoles Part I" edited by W. J. Houlihan pp. 232–317] thermally or preferably in the presence of an acid condensing agent, advantageously a hydrogen halide, e.g. ethanolic hydrogen chloride, or polyphosphoric acid, optionally in an inert solvent preferably at a temperature of about 50°–100° C.

The intermediate hydrazones of formula VII are either isolated or are preferably prepared in situ by the condensation of a ketone of the formula $ArCOCH_2R_1$, wherein Ar and $R_1$ have the meaning as previously described for the compounds of formula I, with a substituted hydrazine of the formula IX

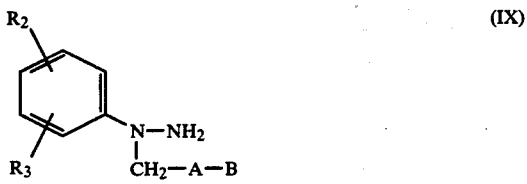

wherein the symbols A, B, $R_2$ and $R_3$ have meaning as previously defined for the compounds of formula I, advantageously in the presence of an acid catalyst.

The starting hydrazines of formula IX are in turn preferably prepared by e.g. nitrosation of the correspondingly substituted anilines of formula X

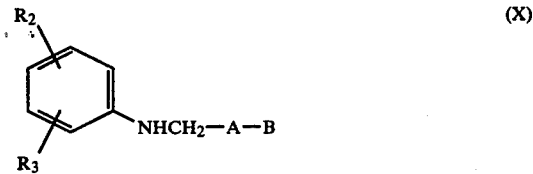

wherein the symbols A, B, $R_2$ and $R_3$ have meaning as previously defined, and subsequent reduction of the N-nitroso derivatives, e.g. with zinc in acetic acid or by other methods well-known to the art.

If said intermediates contain interfering reactive groups, e.g. hydroxy or amino groups, such may advantageously be temporarily protected at any stage with easily removable blocking groups, e.g. in the form of esters or amides respectively, by methods well known to the art.

The cyclization according to process (3) is carried out under conditions of the Madelung indole synthesis as described in "Heterocyclic Compounds, Indoles Part I", edited by W. J. Houlihan, pp. 385–396. The intramolecular cyclization is preferably carried out in the presence of a strong base, e.g. sodium ethoxide, sodium amide, potassium t-butoxide advantageously at elevated temperature e.g. ca. 300° neat or in an inert high boiling solvent such as tetrahydronaphthalene.

The intermediates of formula VIII are prepared by acylation of the substituted anilines with a compound of the formula ArCOOH or a reactive functional derivative thereof.

The compounds of formula I wherein $R_1$ represents hydrogen may also be prepared by decarboxylation of a compound of structural formula I wherein $R_1$ represents carboxy and wherein Ar, A, B, $R_2$ and $R_3$ are as previously defined.

The decarboxylation is carried out in a conventional manner, e.g. with heat in an inert high boiling solvent or in the presence of a strong acid, e.g. a mineral acid such as hydrochloric acid.

The starting 3-carboxy-substituted indoles are prepared according to conventional methods. For example, compounds of formula I, e.g. wherein $R_1$ (the substituent at the 3-position) is carboxy and wherein one of $R_2$ and $R_3$ represents 5-hydroxy, may be prepared according to the Nenitzescu synthesis as described in Heterocyclic Compounds, Indoles Part I page 413, e.g. by condensing p-benzoquinone with a lower alkyl β-pyridyl-β-($CH_2$-A-B-substituted amino)-acrylate, such as ethyl β-(3-pyridyl)-β-(5-ethoxycarbonylpentylamino)-acrylate, and hydrolyzing the resulting lower alkyl ester of the corresponding substituted 5-hydroxy-2-(3-pyridyl)-indole-3-carboxylic acid (a compound of formula I wherein $R_1$ is lower alkoxycarbonyl).

The conversion of a compound of formula Ia according to a process (4) wherein C differs from B into a compound of formula I, and the optional conversion of resulting product of formula I into another compound of this invention are performed by chemical methodology known to the art, and/or e.g. as described herein.

Convertible group C preferably represents trialkoxymethyl, esterified hydroxymethyl, trialkoxymethyl, etherified hydroxymethyl, halomethyl, cyano, 2-oxazolinyl, dihydro-2-oxazolinyl, lower alkanoyloxymethyl, acetyl, methyl, carboxycarbonyl, trihaloacetyl, di(lower)alkoxymethyl, alkylenedioxymethyl, vinyl, alkynyl, esterified carboxy, amidated carboxy.

The intermediates of formula Ia are prepared according to processes 1 to 3 and/or as described herein, using conventional chemical methodology well known to the art.

Certain terms used in the foregoing processes have the meanings as defined below.

Reactive funtional derivatives of alcohols of formula VI or VIa are e.g. such esterified by a strong inorganic or organic acid above all a hydrohalic acid, e.g. hydrochloric, hydrobromic or hydriodic acid, an aliphatic or aromatic sulfonic acid, e.g. methanesulfonic acid, p-toluenesulfonic acid, and are prepared by methods known in the art.

Trialkoxymethyl represents preferably tri(lower alkoxy)-methyl, particularly triethoxy- or trimethoxymethyl.

Etherified hydroxymethyl represents preferably tertiary lower alkyloxymethyl, lower alkoxyalkoxymethyl such as methoxyethyloxymethyl, 2-oxa- or 2-thiacycloalkoxymethyl particularly 2-tetrahydropyranyloxymethyl.

Esterified hydroxymethyl represents preferably lower alkanoyloxymethyl, advantageously acetoxymethyl.

Halomethyl represents especially chloromethyl but may also be bromomethyl or iodomethyl.

An alkali metal represents preferably lithium but may also be potassium or sodium.

Intermediates of formula Ia or Ib wherein C or B' is halomethyl may be reacted preferably with a metal cyanide such as potassium cyanide in a conventional manner to yield the compounds of formula I wherein the chain is extended by 1 carbon atom and B is cyano.

These in turn are converted to compounds of formula I wherein B is carboxy, alkoxycarbonyl or carbamoyl using methods known to the art.

Thus, the compounds of formula Ia or Ib wherein C or B' represents cyano (nitriles) are converted to compounds of formula I wherein B is carboxy by hydrolysis with inorganic acids e.g. a hydrohalic acid such as hydrochloric acid or sulfuric acid in aqueous solution, or advantageously by hydrolysis with aqueous alkali metal hydroxide e.g. potassium hydroxide at reflux temperature.

The conversion of said nitriles to compounds of formula I wherein B represents lower alkoxycarbonyl is advantageously carried out by treatment first with a lower alkanol, e.g. anhydrous ethanol, in the presence of a strong acid, e.g. hydrochloric acid preferably at reflux temperature, followed by careful hydrolysis with water.

Furthermore, the conversion of the said nitriles to compounds of formula I wherein B represents carbamoyl is preferably carried out by treatment with an alkali metal hydroxide, e.g. dilute sodium hydroxide, and hydrogen peroxide, preferably at room temperature.

Furthermore, the intermediates of formula Ia or Ib wherein C or B' is halomethyl, such as chloromethyl, are converted to compounds of formula I, wherein B is carboxy and the chain length is extended by two carbons, by first treating with e.g. a di-(lower) alkyl malonate, such a diethyl malonate, in the presence of a base such as potassium carbonate or sodium ethoxide, in a solvent such as dimethylformamide, preferably at a temperature range from 50° to 100°. The resulting substituted di(lower)alkyl malonate is hydrolyzed, advantageously with aqueous base, such as dilute sodium hydroxide, to the corresponding malonic acid which is decarboxylated under standard conditions, e.g. by heating in xylene solution, to give a compound of formula I wherein B is carboxy. Substitution of the di-(lower)alkyl malonate with a lower alkyl cyanoacetate yields the corresponding compounds of formula Ia or Ib wherein C or B' is cyano.

Compounds of the invention, whrein A represents straight chain or branched alkenylene with a terminal double bond, may also be prepared from intermediates of formula Ia or Ib wherein C or B' is halomethyl. For instance, said intermediates are first treated with e.g. a lower alkyl ester of an α-(aryl- or alkyl) thioacetic acid such as ethyl α-(phenylthio)- acetate, in the presence of a strong base such as sodium hydride. Subsequent oxidation of the resulting α-arylthio or αalkylthio substituted ester to the α-arylsulfinyl or α-alkylsulfinyl ester with e.g. sodium periodate, followed by heat-induced elimination, by e.g. refluxing in xylene, yields a compound of general formula I (an α,β-unsaturated ester) wherein A represents alkenylene and B represents e.g. lower alkoxycarbonyl, and the chain length has been extended by two carbon atoms. The same transformation is also carried out using e.g. ethyl α-(phenylseleno)acetate as described in J. Am. Chem. Soc. 95, 6137(1973). Similarly, the compounds of formula Ia wherein C represents halomethyl may first be converted to the corresponding carboxaldehydes with e.g. dimethylsulfoxide in the presence of triethylamine and silver tetrafluoroborate, or with chromium trioxide and pyridine in methylene chloride. Subsequent Wittig condensation e.g. with trimethylphosphonoacetate or ethyl (triphenylphosphorarylidene)acetate also yields the above-cited α,β-unsaturated esters.

Compounds of formula I wherein B is lower alkoxycarbonyl may be amidized with ammonia, mono- or di-(lower) alkylamines e.g. methylamine, dimethylamine in an inert solvent, e.g. a lower alkanol, such as butanol, optionally at elevated temperatures to yield compounds of formula I wherein B represents unsubstituted, mono- or di(lower) alkylcarbamoyl.

Compounds of formula I wherein A contains straight chain or branched alkenylene with a terminal double bond, e.g. α,β-unsaturated esters, may also be prepared from the corresponding α,β-saturated compounds by treatment with e.g. phenylselenyl chloride in the presence of a strong base according to the procedure described in J. Am. Chem. Soc. 95, 6137 (1973).

Conversion of compounds of formula I wherein B is lower alkoxycarbonyl; cyano; unsubstituted, mono- or di-(loweralkyl) carbamoyl to compounds of formula I wherein B represents carboxy is advantageously carried out by hydrolysis with inorganic acids such as hydrohalic or sulfuric acid or with aqueous alkalies, preferably alkali metal hydroxides such as lithium or sodium hydroxide.

Compounds of formula I wherein B represents carboxy or lower alkoxycarbonyl may be reduced with simple or complex light metal hydrides such as lithium aluminum hydride, alane or diborane to compounds of formula I wherein B is hydroxymethyl. Said alcohols are also obtained by appropriate solvolysis of compounds of formula Ia wherein C is halomethyl by treatment with e.g. in alkali metal hydroxide such as lithium or sodium hydroxide.

Said alcohols may in turn be transformed to the compounds of formula I wherein B is carboxy with conventional oxidizing agents, advantageously with pyridinum dichromate in dimethylformamide at room temperature.

Free carboxylic acids may be esterified with lower alkanols such as ethanol in the presence of a strong acid, e.g. sulfuric acid, advantageously at elevated temperature or with diazo (lower) alkanes, e.g. diazomethane in a solvent such as ethyl ether, advantageously at room temperature, to give the corresponding esters, namely compounds of formula I wherein B is lower alkoxycarbonyl.

Furthermore, the free carboxylic acids may be converted via treatment of a reactive intermediate thereof, e.g. an acyl halide such as the acid chloride, or a mixed anhydride, e.g. such derived from a lower alkyl halocarbonate such as ethyl chloroformate, with ammonia, mono- or di-(lower) alkylamines, in an inert solvent such as methylene chloride, preferably in the presence of a basic catalyst such as pyridine, to compounds of formula I wherein B represents unsubstituted, mono or di-(lower)alkylcarbamoyl.

Compounds of formula I wherein B represents mono(lower)alkylcarbamoyl are converted to compounds of formula I wherein B is di-(lower)alkyl-carbamoyl by treatment of the former with a strong base e.g. sodium hydride followed by an alkylating agent, e.g. a lower alkyl halide in an inert solvent, e.g. dimethylformamide.

Furthermore compounds of formula I wherein A represents a straight chain or branched alkynylene or alkenylene may be converted by catalytic hydrogenation, advantageously under neutral conditions e.g. with palladium catalyst at atmospheric pressure in an inert solvent, e.g. ethanol, to compounds of formula I wherein A represents straight chain or branched alkylene.

The carboxaldehydes, the compounds of formula I wherein B represents formyl, may be prepared by oxidizing compounds of formula Ia wherein C represents respectively hydroxymethyl or halomethyl with e.g. dimethyl sulfoxide and a catalyst, such as a mixture of triethylamine and silver tetrafluoroborate, or with chromium trioxide and pyridine or other oxidizing agents known in the art. Said carboxaldehydes are converted to the corresponding acetals, the compounds of formula Ia wherein C represents di(lower)alkoxymethyl, or alkylenedioxymethyl e.g. a dimethylacetal, by acid-catalyzed condensation with an alcohol, e.g. methanol.

Compounds of formula I wherein B represents carboxy may be converted by the well-known Arndt-Eistert synthesis to compounds of formula I wherein B represents carboxy and the chain has been extended by 1 carbon atom. More particularly, a reactive functional derivative of the starting carboxylic acid, e.g. the acid chloride, is treated with diazomethane in e.g. diethyl ether to yield a compound of formula Ia wherein C represents diazoacetyl. Rearrangement with e.g. silver oxide yields said carboxylic acid of formula I wherein the chain has been extended by 1 carbon atom.

A specific embodiment of process (4) is for the preparation of compounds of formula I wherein B represents carboxy and comprises converting in a compound of the formula Ia in which C represents a functionally modified carboxyl group, the group C into carboxy, optionally by extending the chain A within its definition.

Groups convertible into a carboxy group are, for example, esterified carboxy groups, carboxy groups in form of their anhydrides, including corresponding groups of asymmetrical and inner anhydrides, amidated carboxy groups, cyano, amidino groups, including cyclic amidino group such as 5-tetrazolyl, iminoether groups, including cyclic iminoether groups, e.g., 2-oxazolinyl or dihydro-2-oxazolinyl groups substituted by lower alkyl, and also methyl, hydroxymethyl, etherified hydroxymethyl, lower alkanoyloxymethyl, thialkoxymethyl, acetyl, trihaloacetyl, halomethyl, carboxycarbonyl (COCOOH), formyl (CHO), di(lower)alkoxymethyl, alkylenedioxymethyl, vinyl, ethynyl or diazoacetyl. Simultaneously with conversion of C into the carboxy group, the chain A can be extended within its definition.

Esterified carboxy groups are preferably carboxy groups in form of the lower alkyl esters, e.g. the methyl, ethyl, n- or i-(propyl or butyl) esters; substituted lower alkyl esters e.g. the ω-amino, ω-mono- or dimethylamino, α-carboxy or α-carbethoxy(ethyl, propyl or butyl) esters; aryl(lower)alkyl esters, e.g. benzyl, (methyl-, methoxy-, chloro-)substituted benzyl, and pyridylmethyl esters; lower alkanoyloxy-(lower)alkyl esters, e.g. pivaloyloxymethyl esters; 3-phthalidyl and (methyl-, methoxy-, chloro-)substituted 3-phthalidyl esters, derived from the corresponding 3-hydroxyphthalides, (hydroxy-, lower alkanoyloxy-, lower alkoxy-) substituted lower alkoxymethyl esters e.g. β-(hydroxy-, acetyloxy-, methoxy-) ethoxymethyl esters; bicycloalkyloxy-carbonyl-(lower) alkyl esters, e.g. those derived from bicyclic monoterpenoid alcohols, such as unsubstituted or lower alkyl substituted bicyclo [2,2-1]heptyloxycarbonyl-(lower)alkyl esters, advantageously bornyloxycarbonylmethyl esters; halo substituted lower alkyl esters, e.g. trichloroethyl or iodoethyl esters.

Amidated carboxy groups are preferably carboxy groups in form of their unsubstituted amides; N-mono or di-lower alkylamides, e.g. mono- or di-methylamides; tertiary amides derived from e.g. pyrrolidine, piperidine or morpholine; α-(lower) carboalkoxy- or carboxy-substituted lower alkylamides, e.g. mono N-(carboethoxymethyl)-amides, and mono N-(carboxymethyl)amides; α-(lower) carboalkoxy or carboxy-substituted aryl(-lower) alkylamides, e.g. (carboethoxy or carboxy) substituted phenethylamides; amino(lower)-alkylamides, e.g. β-aminoethylamides and β-(carbobenzyloxyamino)ethylamides.

The conversion into the carboxy group is accomplished by methods which are known per se, and as described herein and in the examples, e.g., by solvolysis such as hydrolysis or acidolysis as previously described, or by reduction (esterified carboxy groups). For example, a trichloroethyl or 2-iodoethyl ester may be converted into the carboxylic acid by reduction, e.g. with zinc and a carboxylic acid in the presence of water. Benzyl esters or nitrobenzyl esters may be converted into the carboxy group by catalytic hydrogenation, the latter also with chemical reducing agents, e.g., sodium dithionite or with zinc and a carboxylic acid. In addition, tert-butyl esters may also be cleaved with trifluoroacetic acid. During the reduction of the group C, an alkenylene or alkynylene chain A may be converted into the corresponding alkylene chain.

Furthermore, compounds of formula Ia wherein C represents acetyl may be oxidatively cleaved to the corresponding compounds of formula I wherein B represents carboxy by conversion first to a compound of formula Ia wherein C reprsents trihaloacetyl, e.g. tribromo or triiodoacetyl, by treatment e.g. with sodium hypobromite followed by cleavage with e.g. an aqueous base, such as sodium hydroxide.

The starting materials of formula Ia wherein C represents acetyl are in turn prepared from compounds of formula Ia wherein C represents halomethyl by treatment with an alkyl ester of acetoacetic acid, e.g. ethyl acetoacetate, in the presence of a base, e.g. sodium hydride, followed by hydrolysis with a strong base, e.g., e.g. aqueous sodium hydroxide.

Said compounds are also prepared by condensing a compound of formula Ia wherein C is cyano with e.g. a Grignard or other organometallic reagent, e.g. methyl magnesium bromide under standard conditions.

Compounds of formula Ia wherein C represents carboxycarbonyl (COCOOH) are converted thermally or by oxidation to compounds of formula I wherein B represents carboxy by heating at elevated temperature e.g., at about 200 degrees, in the presence of glass powder, or by treating e.g., with hydrogen peroxide in the presence of a basic agent, e.g. sodium hydroxide.

The starting materials of formula Ia wherein C represents COCOOH are prepared by e.g. condensation of a compound of formula Ia wherein C represents halomethyl with e.g. 2-ethoxycarbonyl-1,3-dithiane, and subsequent oxidative hydrolysis, e.g. with N-bromosuccinimide in aqueous acetone followed by treatment with dilute aqueous sodium hydroxide.

Compounds of formula Ia wherein C represents formyl, di(lower)alkoxymethyl or alkylenedioxymethyl (formyl protected in the form of an acetal), e.g. the dimethyl acetal, are oxidized with e.g. silver nitrate, pyridinium dichromate or ozone to the corresponding compound of formula I wherein B represents carboxy.

Compounds of formula Ia wherein C represents vinyl may be converted to compounds of formula I wherein B represents carboxy by first ozonolysis to compounds of formula I wherein B represents formyl, which are in turn oxidized to compounds of formula I wherein B represents carboxy.

Compounds of formula Ia wherein C represents vinyl may also be treated with nickel carbonyl and carbon monoxide under high pressure conditions to give compounds of formula I wherein B represents carboxy and the chain A contains a double bond adjacent to the carboxyl group.

Compounds of formula Ia wherein C represents ethynyl may be treated with a strong base, e.g. butyl lithium followed by condensation with carbon dioxide or condensation with a lower alkyl haloformate, e.g. ethyl chloroformate followed by hydrolysis to give compounds of formula I wherein B represents carboxy and the chain A contains a triple bond adjacent to the carboxyl group.

Compounds of formula Ia wherein C represents halomethyl may be converted to a corresponding organometallic intermediate, e.g. a cuprous or magnesium derivative, under conditions well known to the art.

Condensation of e.g. the resulting organomagnesium (Grignard) reagent, e.g. a compound of formula Ia wherein C is transformed to e.g. $CH_2MgCl$, with carbon dioxide yields a compound of formula I wherein B represents carboxy and the chain has been extended by 1 carbon atom.

Condensation of said Grignard reagent with e.g. a lower alkyl haloacetate or e.g. ethyl bromoacetate and subsequent hydrolysis yields a compound of formula I wherein B represents carboxy and wherein the chain has been extended by 2 carbon atoms.

Said Grignard reagent may be condensed in the presence of a cuprous halide, e.g. cuprous chloride, with an $\alpha,\beta$-unsaturated acid, e.g. propiolic or acrylic acid to yield a compound of formula I wherein B represents carboxy and wherein the chain has been extended by 3 carbon atoms.

Furthermore, compounds of formula Ia wherein C represents halomethyl may be condensed with e.g. the 3-lithio derivative of propiolic acid (prepared with e.g. lithium diisopropylamide) to yield a compound of formula I wherein A contains a terminal alkynylene, B represents carboxy and the chain length has been extended by 3 carbon atoms.

Compounds of formula I wherein A represents lower alkylene or a direct bond and B represents hydroxymethyl, as reactive functional derivatives thereof, may be condensed with a lower alkanol (or thiol), or a phenol (or thiophenol) appropriately substituted by B, preferably in the presence of a strong base, to give compounds of formula I wherein A represents lower alkylene-(thio or oxy)-phenylene or lower alkylene-(thio or oxy)-lower alkylene.

The above-mentioned reactions are carried out according to standard methods, in the presence or absence of diluents, preferably such as are inert to the reagents and are solvents thereof, of catalysts, condensing or said other agents respectively and/or inert atmospheres, at low temperatures, room temperature or elevated temperatures preferably at the boiling point of the solvents used, and at atmospheric or super-atmospheric pressure. The preferred solvents, catalysts and reaction conditions are set forth in the appended illustrative examples.

The invention further includes any variant of the present processes, in which an intermediate product obtainable at any stage thereof is used as starting material and the remaining steps are carried out, or the process is discontinued at any stage thereof, or in which the starting materials are formed under the reaction conditions, or in which the reaction components are used in the form of their salts or optically pure antipodes. Mainly those starting materials should be used in said reactions, that lead to the formation of those compounds indicated above as being especially useful.

The invention also relates to novel staring materials and processes for their manufacture.

Depending on the choice of starting materials and methods, the new compounds may be in the form of one of the possible isomers or mixtures thereof, for example, depending on the presence of a double bond and the number of asymmetrical carbon atoms, as pure optical isomers, such as antipodes, or as mixtures of optical isomers such as racemates, mixtures of diastereoisomers, mixtures of racemates or mixtures of geometrical isomers. The aforesaid possible isomers or mixtures thereof are within the purview of this invention; certain particular isomers may be preferred.

Any resulting mixtures of diastereoisomers, mixtures of racemates and geometric isomers can be separated on the basis of the physicochemical differences of the constituents, in known manner, into the pure isomers, diastereoisomrs, racemates, or geometric isomers, for example by chromatography and/or fractional crystallisation.

Any resulting racemates can be resolved into the optical antipodes by known methods, for example by e.g. reacting an acidic end product with an optically active base that forms salts with the racemic acid, and separating the salts obtained in this manner, for example by fractional crystallization, into the diastereoisomeric salts from which the optically active carboxylic acid antipodes can be liberated on acidification. The basic racemic products can likewise be resolved into the optical antipodes, e.g. by separation of the diastereoisomeric salts thereof, with an optically active acid, and liberating the optically active basic compound by treatment with a standard base. Racemic products of the invention can thus be resolved into their optical antipodes, e.g., by the fractional crystallization of d- or l-(tartrates, mandelates, camphorsulfonates), or of d- or l-($\alpha$-methylbenzylamine, cinchonidine, cinchonine, quinine, quinidine, ephedrine, dehydroabietylamine, brucine or strychnine) salts. Advantageously, the more active of the two antipodes is isolated.

Finally the compounds of the invention are either obtained in the free form, or as a salt thereof. Any resulting base can be converted into a corresponding acid addition salt, preferably with the use of a therapeutically useful acid or anion exchange preparation, or resulting salts can be converted into the corresponding free bases, for example, with the use of a stronger base, such as a metal or ammonium hydroxide or a basic salt, e.g. an alkali metal hydroxide or carbonate, or a cation exchange preparation. A compound of formula I wherein B represents carboxy can thus also be converted into the corresponding metal or ammonium salts. These or other salts, for example, the picrates, can also be used for purification of the bases obtained; the bases are converted into salts, the salts are separated and the bases are liberated from the salts. In view of the close relationship between the free compounds and the compounds in the form of their salts, whenever a compound is referred to in this context, a corresponding salt is also intended, provided such is possible or appropriate under the circumstances.

The compounds, including their salts, can also be obtained in the form of their hydrates, or include other solvents used for their crystallization.

The pharmaceutical compositions according to the invention are those suitable for enteral, such as oral or rectal, and parenteral administration to mammals, including man, for the treatment of prevention of diseases responsive to inhibition of thromboxane synthetase, comprising an effective amount of a pharmacologically active compound of formula I, or a pharmaceutically acceptable salt thereof, alone or in combination with one or more pharmaceutically acceptable carriers.

The pharmacologically active compounds of the invention are useful in the manufacture of pharmaceutical compositions comprising an effective amount thereof in conjunction or admixture with excipients or carriers suitable for either enteral or parenteral application. Preferred are tablets and gelatin capsules comprising the active ingredient together with (a) diluents, e.g. lactose, dextrose, sucrose, mannitol, sorbitol, cellulose and/or glycine; (b) lubricants, e.g. silica, talcum, stearic acid, its magnesium or calcium salt and/or polyethyleneglycol; for tablets also (c) binders, e.g. magnesium aluminum silicate, starch paste, gelatin, tragacanth, methylcellulose, sodium carboxymethylcellulose and/or polyvinylpyrrolidone; if desired (d) disintegrants, e.g. starches, agar, alginic acid or its sodium salt, or effervescent mixtures; and/or (e) absorbents, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1 to 75%, preferably about 1 to 50%, of the active ingredient. A unit dosage for a mammal of about 50 to 70 kg may contain between about 10 to 100 mg of the active ingredient.

The following examples are intended to illustrate the invention and are not to be construed as being limitations thereon. Temperatures are given in degrees Centigrade, and all parts wherever given are parts by weight. If not mentioned otherwise, all evaporations are performed under reduced pressure, preferably between about 15 and 100 mmHg.

EXAMPLE 1

Dimethylformamide (1640 ml) is charged into a 20 gallon glass kettle along with 430g of potassium t-butoxide. This solution is stirred under nitrogen and cooled to −8°. A solution of 682 g of 3-methyl-2-(3-pyridyl)indole in 3280 ml of dimethylformamide is added over 0.75 hour while the temperature is maintained below 0°. After 2 hours of stirring of −10°, 1640 ml of a solution of 780 g of methyl 8-bromooctanoate in dimethylformamide is added over 1 hour. Reaction temperature is maintained below 0°. After 2 hours stirring, the reaction mixture is allowed to warm to room temperature overnight. The rust-colored mixture is then cooled to about 5° and treated with 19.7 L of ice water. The temperature rises to 25°. After 0.5 hour stirring, the mixture is extracted with 2×8 L of ether. The extracts are dried (MgSO$_4$) and concentrated in vacuo to give 1-(7-methoxycarbonylheptyl)-3-methyl-2-(3-pyridyl)indole as an oil; 1293 g of this oil is treated with 6.53 L of 1N NaOH and warmed over steam to 90° for 2.5 hours. After cooling to room temperature, the solution is washed with 3×3 L of ether. The aqueous layer is cooled to 10° and acidified to pH 3.5 with 3.4 L of 2N HCl. The heavy suspension which results is extracted with 4×4 L of methylene chloride. The combined extracts are washed once with 4 L of water and dried (MgSO$_4$). After filtration and evaporation of solvent in vacuo at 60°, the residue is triturated with ether (2.0 L) and dried to give 1-(7-carboxyheptyl)-3-methyl-2-(3-pyridyl)indole, m.p. 113°-115°. Recrystallization from ethanol raises melting point to 114°-116°.

The starting 3-methyl-2-(3-pyridyl)indole is prepared essentially as described in U.S. Pat. No. 3,468,894.

Methyl 8-bromooctanoate is prepared from azelaic acid essentially as described in U.S. Pat. No. 3,852,419, or by direct esterification of 8-bromooctanoic acid as follows:

Methanol (4.7 L), 8-bromooctanoic acid (0.912 kg) and sulfuric acid (0.912 L) are charged into a suitable reactor and the mixture is heated at reflux temperature for 5 hours and is then stirred at ambient temperature overnight. The solvent is removed at reduced (3 mm Hg) pressure and the oily residue is dissolved in ether (4 L). The solution is washed with water (3×2 L), saturated NaHCO$_3$ solution (1 L) and brine (1 L). The ether portion is dried (MgSO$_4$) and filtered to remove dessicant. Evaporation of solvent followed by distillation of the crude oil gives methyl 8-bromooctanoate, b.p. 73°-76°/0.05 mm Hg, n$_D^{23}$ 1.4614.

EXAMPLE 2

To a suspension of 4.8 g of 50% sodium hydride (dispersion in mineral oil) in 40 ml of dimethylformamide under nitrogen is added dropwise a solution of 13.5 g of 3-methyl-2-(3-pyridyl)indole in 80 ml of dimethylformamide. After addition is completed, the greenish yellow mixture is stirred at room temperature for about 1 hour. Ethyl bromoacetate (11.2 ml, 0.10 mole) is added dropwise to the reaction mixture which is cooled to 0°-5°, and the resulting reaction mixture is stirred at room temperature for 4 hours.

The reaction mixture is poured into 1 L of ice-water and is extracted with 3×300 ml of ether. The ether layer is extracted with 3×300 ml of 1 N hydrochloric acid. The acidic extract is adjusted to pH 9-10 with concentrated ammonium hydroxide and extracted with 3×250 ml of ether. The combined ether extracts are dried (MgSO$_4$), filtered, and concentrated under vacuum to give 1-ethoxycarbonylmethyl-3-methyl-2-(3-pyridyl)indole as an oil.

This oil is heated at reflux for 4 hours in 500 ml of 1N hydrochloric acid. After standing at room temperature overnight a yellow solid is collected and dried at 60°-80°/30 mm for 12 hours. Recrystallization from ethanol gives 1-carboxymethyl-3-methyl-2-(3-pyridyl)indole hydrochloride, m.p. 204°-207°.

If the free amino acid is desired, it may be obtained by adjusting the pH of the hydrolysis medium to pH 3.5.

EXAMPLES 3-6

Utilizing the procedures of examples 1 and 2, the following compounds of formula II in which $R_1'=CH_3$, $R_2'$ and $R_3'=H$, and $R_4=OH$ are prepared:

| Example | Starting Ester | $C_mH_{2m}$ | Pyr | M.P., °C. | Recrystallization Solvent |
|---|---|---|---|---|---|
| 3 | Br(CH$_2$)$_5$COOEt | (CH$_2$)$_5$ | 3-pyridyl | 113–4 | acetonitrile |
| 4 | Br(CH$_2$)$_6$COOMe | (CH$_2$)$_6$ | 3-pyridyl | 106–7.5 | acetonitrile |
| 5 | Br(CH$_2$)$_4$COOMe | (CH$_2$)$_4$ | 3-pyridyl | 123–5 | ethanol |
| 6 | Br(CH$_2$)$_5$COOEt | (CH$_2$)$_5$ | 4-pyridyl | 186–8 | acetonitrile |

The starting 2-(3- and 4-pyridyl)-indoles are prepared according to U.S. Pat. No. 3,468,894.

The starting ethyl or methyl ω-bromo esters are obtained commercially or are prepared from the commercially available ω-bromoacids as illustrated below for methyl 6-bromohexanoate. A solution of 6-bromohexanoic acid (10 g) in 50 ml of methanol to which is added 1.0 ml of concentrated sulfuric acid is heated under reflux for 8 hours. The methanol is distilled off, the residue is dissolved in ether. The ether solution is washed free of acid with water, dried over sodium sulfate and evaporated to dryness. Distillation at 0.8 mm Hg gives methyl 6-bromohexanoate, b.p. 85°–90°/0.8 mm.

1-(7-Carboxyheptyl)-3-methyl-2-(2-pyridyl)indole is prepared analogous to the procedure of example 1 using as starting material the 3-methyl-2-(2-pyridyl)indole described in J. Chem. Soc. 1955, 2865.

The corresponding compounds of formula II wherein $R_1'$=hydrogen, Pyr=2-,3-, or 4-pyridyl and $R_2'$=fluoro, hydrogen or methyl, and $R_3'$=hydrogen are similarly prepared, using the procedures of examples 1 and 2, from the prerequisite ω-bromo ester and the following known starting 2-(pyridyl)indoles: the 2-(2-,3- and 4-pyridyl)indoles described in Pharm. Bull. Japan 4, 16 (1956); and 5-(fluoro and methyl)-2-(3-pyridyl)indoles described in Bull. Soc. Chim. France 1969, 4154.

EXAMPLES 7 AND 8

The following compounds of formula II in which $R_1'=CH_3$; $R_3'=H$; Pyr=3-pyridyl; $C_mH_{2m}=(CH_2)_5$ and $R_4=OH$ are prepared using analogous procedures to those described in previous examples.

| Example | $R_2'$ | M.P., °C. | Salt |
|---|---|---|---|
| 7 | 5-Cl | 143–5 | — |
| 8 | 5-OCH$_3$ | 175–8 | HCl |

The compound of example 7 is prepared as follows:

To a suspension of 1.39 g of 50% sodium hydride (dispersion in mineral oil) in 30 ml of dimethylformamide is added under nitrogen at 0°–5° dropwise while stirring a solution of 6.59 g of 5-chloro-3-methyl-2-(3-pyridyl)-indole (prepared as described in U.S. Pat. No. 3,468,894) in 60 ml of dimethylformamide. After addition is complete the suspension is stirred at 0° for ½ hour. While maintaining the temperature at 0° a solution of 6.06 g of methyl 6-bromohexanoate in 10 ml of dimethylformamide is added dropwise. The reaction mixture is allowed to reach room temperature and is stirred at room temperature for 5 hours, and poured into 400 ml of ice water. The resulting mixture is extracted with ethyl acetate (3×300 ml). The ethyl acetate extract is washed with saturated sodium chloride solution, dried over magnesium sulfate and evaporated to dryness to give 1-(5-methoxycarbonylpentyl)-5-chloro-3-methyl-2-(3-pyridyl)indole as an oil.

A solution of 3.2 g of the above ester in 30 ml of 3 N sodium hydroxide is heated under reflux for 17 hours. After cooling, the resulting product is collected by filtration, and dissolved in 50 ml of water. Acidification with 2N HCl to pH 4–5 precipitates the product which is purified by suspending in ether to give 1-(5-carboxypentyl)-5-chloro-3-methyl-2-(3-pyridyl)indole, m.p. 143°–145°.

Similarly prepared is 1-(5-carboxypentyl)-5-methoxy-3-methyl-2-(3-pyridyl)indole, obtained as an oil. Treatment with ethanolic hydrochloric acid in ethanol and crystallization by addition of ethyl ether yields the compound of example 8, namely 1-(5-carboxypentyl)-5-methoxy-3-methyl-2-(3-pyridyl)indole hydrochloride, m.p. 175°–178°.

1-(5-carboxypentyl)-5-hydroxy-3-methyl-2-(3-pyridyl)-indole is prepared as follows:

A solution of 1.70 g of 1-(5-carboxypentyl)-5-methoxy-3-methyl-2-(3-pyridyl)indole in 85 ml of 48% hydrobromic acid is heated under reflux for 0.5 hour. The reaction mixture is evaporated to dryness, diluted with water and adjusted to pH 6 with dilute sodium hydroxide. The precipitate is collected and recrystallized from acetone-ether to yield 1-(5-carboxypentyl)5-hydroxy-3-methyl-2-(3-pyridyl)indole.

EXAMPLES 9 AND 10

The following examples of formula III in which $C_pH_{2p}$ represents $CH_2CH_2$, and Pyr represents 3-pyridyl are prepared essentially according to the procedure of example 2. Condensation of ethyl 3-methyl-2-(3-pyridyl)-indole-5-propionate with ethyl 6-bromohexanoate and methyl 8-bromooctanoate respectively yields the esters of examples 9a and 10a. Hydrolysis with hydrochloric acid gives the resulting diacids of examples 9 and 10.

| Example | $C_nH_{2n}$ | M.P., °C. | $R_5$ | $R_6$ | Recrystallization Solvent |
|---|---|---|---|---|---|
| 9a | (CH$_2$)$_5$ | oil | OC$_2$H$_5$ | OC$_2$H$_5$ | — |
| 9 | (CH$_2$)$_5$ | 143–5 | OH | OH | acetonitrile |
| 10a | (CH$_2$)$_7$ | oil | OCH$_3$ | OC$_2$H$_5$ | — |
| 10 | (CH$_2$)$_7$ | 128–30 | OH | OH | acetonitrile |

1-(7-carboxyheptyl)-3-methyl-2-(4-pyridyl)-indole-5-propionic acid is similarly prepared.

The starting indoles are prepared as follows:

To a suspension of p-hydrazinohydrocinnamic acid (Manske and Kulka, J. Can. Res., 25B: 376 (1947), 4.50 g) in 50 ml of absolute ethanol under nitrogen at room temperature is added while stirring 10 ml of a saturated ethanolic hydrogen chloride solution. A solution results in approximately 5 minutes. To the red-orange solution is added 3-propionylpyridine (3.37 g, 0.025 mole), the reaction mixture is heated to reflux and maintained at reflux for 18 hours. The resulting solution is cooled in an ice-water bath and the resulting yellow crystals of ethyl 3-methyl-2-(3-pyridyl)indole-5-propionate hydrochloride are collected, m.p. 249°–251°. The free base, ethyl 3-methyl-2-(3-pyridyl)indole-5-propionate is prepared by suspending the hydrochloride salt in water, basifying with 3N sodium hydroxide and extracting with ether.

Similarly prepared is ethyl 3-methyl-2-(4-pyridyl)-indole-5-propionate hydrochloride, m.p. greater than 275°, and the corresponding free base.

Heating a suspension of 7.5 g of ethyl 3-methyl-2-(3-pyridyl)indole-5-propionate hydrochloride in 450 ml of 2N HCl at reflux temperature for 2 hours, cooling and collecting the resulting solid gives 3-methyl-2-(3-pyridyl)-indole-5-propionic acid hydrochloride, m.p. 290°. Similar hydrolysis of ethyl 3-methyl-2-(4-pyridyl)indole-5-propionate yields 3-methyl-2-(4-pyridyl)indole-5-propionic acid hydrochloride, melting above 305°.

EXAMPLE 11

(a) A solution of 1-(4-cyanobenzyl)-3-methyl-2-(3-pyridyl)indole 5.8 g) in 100 ml of a 1:1 mixture of 20% aqueous hydrochloric acid and glacial acetic acid is heated at reflux for 20 hours. After cooling, the solution is poured into ice water (100 ml) and the pH is adjusted to 4.5–5 with saturated sodium bicarbonate solution. The resulting precipitate is extracted with ethyl acetate, the ethyl acetate extract is washed with water and evaporated to dryness to give 1-(4-carboxybenzyl)-3-methyl-2-(3-pyridyl)indole, m.p. 273°–275°.

The starting nitrile is prepared as follows:

To a suspension of 2.9 g (0.06 mole) of 50% sodium hydride in mineral oil in 40 ml of dimethylformamide under nitrogen at 0°–5° is added dropwise over 20 minutes a solution of 10.4 g (0.05 mole) of 3-methyl-2-(3-pyridyl)indole in 60 ml of dimethylformamide. The reaction mixture is stirred for 0.5 hour at 0°–5° followed by dropwise addition of 9.8 g (0.05 mole) of p-cyanobenzyl bromide in 50 ml of dimethylformamide. After stirring at 0°–10° for 1 hour and at room temperature for 0.5 hour, the reaction mixture is poured into ice-water (600 ml). The resulting solid is collected, dried, washed with petroleum ether and redissolved in ether (500 ml). The ether solution is first washed with water, then with saturated sodium bicarbonate solution, dried over MgSO₄, treated with charcoal and filtered. Evaporation of the ether extract to dryness yields a yellow solid. This product is slurried in hot cyclohexane and collected by filtration to give 1-(4-cyanobenzyl)-3-methyl-2-(3-pyridyl)indole, m.p. 127°–129°.

(b) Similarly prepared is 1-(4-carboxybenzyl)-5-chloro-3-methyl-2-(3-pyridyl)-indole hydrochloride, m.p. 217°–220°.

EXAMPLE 12

(a) To a suspension of 0.49 g of lithium aluminum hydride in 50 ml of anhydrous tetrahydrofuran under nitrogen is added dropwise at room temperature a solution of 3.92 g of 1-(5-methoxycarbonylpentyl)-5-chloro-3-methyl-2-(3-pyridyl)indole in 30 ml of anhydrous tetrahydrofuran. After addition is complete the suspension is stirred for 1 hour at room temperature, and 50 ml of a saturated ammonium chloride solution is added. The reaction mixture is allowed to stand at room temperature overnight and the organic layer is separated. The aqueous layer is filtered to remove salts and extracted with ethyl acetate (2×50 ml). The combined organic layers are washed with saturated brine, dried over magnesium sulfate and concentrated in vacuo. The crude product is purified by trituration with hexane/ether and dissolved in ethanol. Ethanolic hydrochloric acid is added to acidity and the solution diluted with anhydrous ether to crystallize the product. 1-(6-Hydroxyhexyl)-5-chloro-3-methyl-2-(3-pyridyl)indole hydrochloride hemihydrate, m.p. 115°–118°, is obtained.

(b) Similarly prepared is 1-(6-hydroxyhexyl)-3-methyl-2-(3-pyridyl) indole as an oil; NMR (CDCl₃) δ3.50 (t,2H), 3.98 (t,2H).

EXAMPLE 13

To a suspension of 1.52 g of 1-(5-carboxypentyl)-5-chloro-3-methyl-2-(3-pyridyl)indole in 50 ml of toluene under nitrogen is added dropwise at room temperature 0.31 ml of thionyl chloride. The resulting mixture is heated under reflux for 1 hour. An additional 0.10 ml portion of thionyl chloride is added and the solution is stirred at room temperature overnight. The resulting suspension is evaporated to dryness to give crude 1-(5-chlorocarbonylpentyl)-5-chloro-3-methyl-2-(3-pyridyl)indole which is used directly without further purification. A suspension of 0.86 g of the above 1-(5-chlorocarbonylpentyl)-5-chloro-3-methyl-2-(3-pyridyl)indole in 20 ml of concentrated ammonium hydroxide is stirred at room temperature overnight. Filtration of the suspension and slurrying of the resulting solid in ethyl ether yields 1-(5-carbamoylpentyl)-5-chloro-3-methyl-2-(3-pyridyl)indole, m.p. 137°–140°.

EXAMPLE 14

To a suspension of 2.9 g (0.06 mole) of 50% sodium hydride in mineral oil in 40 ml of dimethylformamide under nitrogen at 0°–5° is added dropwise over 20 minutes a solution of 10.4 g of 3-methyl-2-(3-pyridyl)indole in 60 ml of dimethylformamide. The mixture is stirred for 0.5 hour at 0°–5° followed by the dropwise addition of 17.6 g (0.06 mole) of 1-tetrahydropyranyloxy-8-bromooctane in 50 ml of dimethylformamide. After stirring at 0°–10° for 1 hour and at room temperature for 0.5 hour, the reaction mixture is poured into ice-water and extracted with ether. The ether extract is washed with water, dried over MgSO₄ and evaporated to dryness. The residue is dissolved in 100 ml of 3N hydrochloric acid, the resulting mixture is kept at room temperature for 0.5 hour, washed with ether, basified with aqueous with 3N sodium hydroxide solution and extracted with methylene chloride. The methylene chloride solution is evaporated to dryness to give 1-(8-hydroxyoctyl)-2-(3-pyridyl)-3-methylindole.

EXAMPLE 15

A solution of 4 g of 1-(7-methoxycarbonylheptyl)-3-methyl-2-(3-pyridyl)indole in 40 ml of n-butanol is saturated with methylamine and heated on a steam bath in a pressure bottle for 3 days. The reaction mixture is evaporated to dryness and the product is crystallized from ethyl-ether to yield the 1-[7-(N-methylcarbamoyl)heptyl]-3-methyl-2-(3-pyridyl)indole.

EXAMPLE 16

Preparation of 10,000 tablets each containing 10 mg of the active ingredient of Example 1:

| Formula: | |
|---|---|
| 1-(7-carboxyheptyl)-3-methyl-2-(3-pyridyl)indole | 100.00 g |
| Lactose | 1,157.00 g |
| Corn starch | 75.00 g |
| Polyethylene glycol 6,000 | 75.00 g |
| Talcum powder | 75.00 g |
| Magnesium stearate | 18.00 g |
| Purified water | q.s. |

Procedure:

All the powders are passed through a screen with openings of 0.6 mm. Then the drug substance, lactose, talcum, magnesium stearate and half of the starch are mixed in a suitable mixer. The other half of the starch is suspended in 40 ml of water and the suspension added to the boiling solution of the polyethylene glycol in 150 ml of water. The paste formed is added to the powders which are granulated, if necessary, with an additional amount of water. The granulate is dried overnight at 35°, broken on a screen with 1.2 mm openings and compressed into tablets using concave with 6.4 mm diameter, uppers bisected.

EXAMPLE 17

Preparation of 10,000 capsules each containing 25 mg of the active ingredient of Example 11a:

| Formula: | |
|---|---|
| 1-(4-carboxybenzyl)-3-methyl-2-(3-pyridyl)indole | 250.0 g |
| Lactose | 1,650 g |
| Talcum powder | 100.0 g |

Procedure:

All the powders are passed through a screen with openings of 0.6 mm. Then the drug substance is placed in a suitable mixer and mixed first with the talcum, then with the lactose until homogenous. No. 3 capsules are filled with 200 mg, using a capsule filling machine.

Similarly prepared are tablets and capsules comprising about 10–100 mg of other compounds of the invention, e.g. of 1-(5-carboxypentyl)-5-(chloro, fluoro, methoxy or methyl)-3-methyl-2-(3-pyridyl)indole, 1-(5-carboxypentyl)-5,6-dichloro-3-methyl-2-(3-pyridyl)indole, or any other compound given in the examples herein.

EXAMPLE 18

A solution of 50 mg of 1-(5-carbamoylpentyl)-5-chloro-3-methyl-2-(3-pyridyl)indole in 1 ml of 6 N HCl is heated at reflux temperature for 3 hours. On cooling the hydrochloride salt precipitates. The suspension is concentrated to dryness and the residue basified with saturated NaHCO$_3$ solution. This solution is washed with ether and neutralized to pH 6-7 with 2 N HCl. The crude free acid, 1-(5-carboxypentyl)-5-chloro-3-methyl-2-(3-pyridyl)indole, m.p. 137°-141°, is obtained.

EXAMPLE 19

To a mixture of 4.17 g of 3-methyl-2-(3-pyridyl)indole, 0.64 g of tetra-n-butyl ammonium bromide and 1.2 g of powdered KOH in 500 ml of acetonitrile, while stirring at room temperature under nitrogen, is added 5.06 g of ethyl p-(2-bromoethoxy)benzoate [for preparation see U.S. Pat. No. 2,790,825 (1957)]. The suspension is stirred for five days. After filtration to remove KBr, the filtrate is concentrated to an oil which is dissolved in ethyl acetate and extracted with 3 N HCl. The acid layer is separated and treated with 3 N NaOH. This suspension is extracted with ethyl acetate (3×100 ml) and the organic extract is separated, dried over MgSO$_4$, and concentrated to give as an oil 1-[2-(4-ethoxycarbonylphenoxy)ethyl]-2-(3-pyridyl)-3-methylindole.

EXAMPLE 20

A mixture of 4.7 g of 1-[2-(4-ethoxycarbonylphenoxy)ethyl]-2-(3-pyridyl)-3-methylindole in 220 ml of 2N hydrochloric acid is heated under reflux for 6 hours. After cooling the solution is made basic with 3 N NaOH and extracted with ethyl acetate. The basic solution is filtered and acidified to pH 6-7 with 5 N HCl. The solid is collected, dried and recrystallized from acetone to give 1-[2-(4-carboxyphenoxy)ethyl]-2-(3-pyridyl)-3-methylindole, m.p. 190°-193°.

EXAMPLE 21

A solution of 5.9 g of p-mercaptobenzoic acid ethyl ester (prepared according to the procedure found in J. Chem. Soc., 1963, 1947–1954) in 30 ml of dimethylformamide is added dropwise to a slurry of 1.55 g of 50% sodium hydride (dispersion in mineral oil in 30 ml of dimethylformamide. This mixture is stirred at room temperature for 0.5 hour under nitrogen atmosphere. This solution is added dropwise to a solution of 9.78 g of 1-(2-methylsulfonyloxyethyl)-2-(3-pyridyl)-3-methylindole in 60 ml of dimethylformamide at −10°. This mixture is stirred at room temperature overnight and poured into 1 liter of ice-water. This is extracted several times with ether (ca 1 liter total). The ether extract is washed with water (3×200 ml), dried over MgSO$_4$ and evaporated in vacuo yielding 1-[2-(4-ethoxycarbonylphenylthio)ethyl]-2-(3-pyridyl)-3-methylindole as an oil; NMR (CDCl$_3$) confirms the structure.

The starting material is prepared as follows:

To 11.77 g of 1-(2-ethoxycarbonylmethyl)-2-(3-pyridyl)-3-methylindole in 400 ml of dry tetrahydrofuran at 0° is added 60 ml of a 1 M solution of lithium aluminum hydride in tetrahydrofuran. This is allowed to stir at room temperature for 1 hour, then cooled by an ice bath and quenched successively with 2.26 ml of water, 2.26 ml of a 15% sodium hydroxide solution, and 6.78 ml of water. The mixture is filtered, concentrated in vacuo, and the residue dissolved in ether, washed with a saturated NaHCO$_3$ solution, dried over MgSO$_4$ and concentrated in vacuo. There is obtained the semi-solid 1-(2-hydroxyethyl)-2-(3-pyridyl)-3-methylindole which is used directly in the next step.

Methanesulfonyl chloride (2.70 ml) is added dropwise to a solution of 7.5 g 1-(2-hydroxyethyl)-2-(3-pyridyl)-3-methylindole and 10.34 ml of triethylamine in 150 ml of methylene chloride at −10°. This mixture is stirred at room temperature for 0.5 hour and poured into 600 ml of ice water. The resulting slurry is extracted with methylene chloride and the extract is washed with saturated NaHCO$_3$ solution, dried over MgSO$_4$ and evaporated in vacuo. There is obtained 1-(2-methylsulfonyloxyethyl)-2-(3-pyridyl)-3-methylindole which is used directly in the above reaction.

EXAMPLE 22

A mixture of 6.39 g of 1-[2-(4-ethoxycarbonylphenylthio)ethyl]-2-(3-pyridyl)-3-methylindole in 260 ml of 2 N HCl is heated at reflux temperature for 6 hours. After cooling the pH is adjusted to 6–7 with saturated aqueopus NaHCO$_3$ (ca 500 ml). About 200 ml of ether is added and the mixture is stirred for 0.5 hour. A solid is collected, first washed with water, then ether, and then dissolved in 100 ml hot absolute ethanol. The solution is filtered, and while still hot treated with 1.68 ml of 6.5 N ethanolic HCl. The solution is cooled and diluted with ca 100 ml ether. The resulting product is collected to yield 1-[2-(4-carboxyphenylthio)ethyl]-2-(3-pyridyl)-3-methylindole hydrochloride, m.p. 222°–224°.

EXAMPLE 23

A solution of lithium diisopropylamide (LDA) is prepared by adding n-butyl lithium (7.66 mmol, 1.6M in hexane) to a solution of diisopropylamine (7.6 mmol) in tetrahydrofuran (THF, 12 ml) at −20°. The LDA solution is cooled to −78° and 1-(5-methoxycarbonylpentyl)-2-(3-pyridyl)-3-methylindole (2.48 g) in THF (24 ml) is added dropwise over 5 minutes. The mixture is stirred at −78° for 20 minutes, followed by addition of phenylselenyl chloride (1.5 g) in THF (12 ml). After 5 minutes the cooling bath is removed and the mixture allowed to warm to 0°. Saturated aqueous sodium bicarbonate (60 ml) is added, followed by ether extraction (3×50 ml). The combined organic phases are washed with saturated aqueous sodium bicarbonate, brine and then dried over anhydrous magnesium sulfate. Concentration in vacuo gives the crude 1-(5-methoxycarbonyl-5-phenylselenylpentyl)-2-(3-pyridyl)-3-methylindole as a yellow oil. The crude selenide is dissolved in dichloromethane (40 ml) and 30% hydrogen peroxide (1.8 g, 16 mmol) in water (1.8 ml) is added dropwise. An exotherm begins after the addition of ca. 10% of the hydrogen peroxide. The temperature rises to 30° by completion of the addition. Stirring is continued for an additional 30 minutes, then 5% aqueous sodium carbonate (40 ml) is added. The dichloromethane layer is separated. The aqueous phase is extracted with dichloromethane (25 ml). The combined organic phases are washed with 5% aqueous sodium carbonate, water, brine, and dried over anhydrous magnesium sulfate. Concentration in vacuo yields 1-(5-methoxycarbonyl-pent-4-enyl)-2-(3-pyridyl)-3-methylindole as a light yellow oil. Further purification is achieved by flash chromatography (SiO$_2$) using ethyl acetate:hexane (2:3) as the eluent. NMR (CDCl$_3$) δ5.53 (d, 1H), 6.65 (m, 1H); IR (neat) 1720 cm$^{-1}$.

EXAMPLE 24

To a solution of the α,β-unsaturated ester 1-(5-methoxycarbonylpent-4-enyl)-2-(3-pyridyl)-3-methylindole (84 mg) in methanol (1 ml) is added 1 N aqueous lithium hydroxide (1 ml). The mixture is stirred at room temperature overnight, then evaporated to dryness in vacuo. The residue is dissolved in water (2 ml) and washed with diethyl ether (5 ml). The aqueous phase is acidified to pH 6.6–7.0 and extracted with dichloromethane. The organic extract is washed with brine and dried over magnesium sulfate, then concentrated in vacuo to a pale yellow oil which solidifies upon trituration with chloroform to give 1-(5-carboxypent-4-enyl)-2-(3-pyridyl)-3-methylindole, m.p. 145°–147°.

EXAMPLE 25

To a solution of Collins Reagent prepared with chromium trioxide (5.6 g) and pyridine (8.86 g, 112 mmol) in dichloromethane (150 ml) at 0°–5° under a nitrogen atmosphere is added all at once 1.8 g of 1-(6-hydroxyhexyl)-3-methyl-2-(3-pyridyl)-indole in dichloromethane (15 ml). The mixture is stirred for an additional 25 minutes, then filtered through celite. The filtrate is then passed through a silica gel column. The product is eluted from the silica gel with a 1:1 mixture of ethyl acetate:dichloromethane (500 ml). Concentration in vacuo yields the desired 1-(5-formylpentyl)-2-(3-pyridyl)-3-methylindole as a pale yellow oil; NMR (CDCl$_3$) δ9.7 (t, 1H); IR (neat) 2710, 1720 cm$^{-1}$.

EXAMPLE 26

Trimethyl phosphonoacetate (328 mg) is added dropwise to a solution of potassium tert-butoxide (220 mg) in THF (5 ml) of 0° under a nitrogen atmosphere. The solution is stirred at 0° for 10 minutes, then cooled to −78°. A solution of the aldehyde, 1-(5-formylpentyl)-2-(3-pyridyl)-3-methylindole (450 mg) in THF (5 ml) is added dropwise over 15 minutes. The mixture is kept at −78° for 15 minutes, then the cooling bath is removed. The mixture is stirred overnight at room temperature, then diluted with water (25 ml) and extracted with diethyl ether (3×25 ml). The combined extracts are washed with saturated sodium bicarbonate, then brine, and dried over anhydrous magnesium sulfate. Concentration in vacuo yields the desired α,β unsaturated ester 1-(7-methoxycarbonylhept-6-enyl)-2-(3-pyridyl)-3-methylindole as a pale yellow oil; IR (neat) 1735 cm$^{-1}$.

EXAMPLE 27

Hydrolysis of 50 mg of 1-(7-methoxycarbonylhept-6-enyl)-2-(3-pyridyl)-3-methylindole according to the procedure of example 24 yields 1-(7-carboxyhept-6-enyl)-2-(3-pyridyl)-3-methylindole, m.p. 144°–146° (recrystallized from dichloromethane/hexane).

EXAMPLE 28

1-(7-Carboxyhept-6-enyl)-2-(3-pyridyl)-3-methylindole (10 mg) is dissolved in 1 ml of absolute ethanol with a catalytic amount of 10% palladium on charcoal and hydrogenated at 1 atmosphere pressure. After 3.5 hours, the catalyst is removed by filtration and washed with a few milliliters of ethanol. The combined filtrates are concentrated in vacuo to yield a colorless oil which crystallizes to give 1-(7-carboxyheptyl)-3-methyl-2-(3-pyridyl)indole of Example 1 (crude product has m.p. 110°–113°).

EXAMPLE 29

1-(4-Cyanobutyl)-3-methyl-2-(3-pyridyl)-indole (578 mg) is heated at 185° for 0.5 hour with 450 mg of powdered NaOH and 5 ml of ethylene glycol; there is obtained, after pouring the reaction solution into 50 ml water, washing with ether, and adjusting the pH to 6 with 2 N HCl, an oily solid which crystallizes to give 1-(4-carboxybutyl)-3-methyl-2-(3-pyridyl)indole of Example 5 (m.p. 127°–129°).

The starting material is prepared as follows:

A solution of 3-methyl-2-(3-pyridyl)indole (2.09 g) in 12 ml of DMF is added to a suspension of 0.528 g of 50% sodium hydride (dispersion in mineral oil) in 6 ml of DMF at 0°. The mixture is stirred at 0° for 0.5 hour and is treated with a solution of 1.78 g of 5-bromovaleronitrile in 4 ml of DMF. This mixture is stirred at room temperature overnight and is poured into 125 ml of water. This is extracted with 2×50 ml of ether, the extract is washed with 3×20 ml of water and dried over MgSO$_4$ to give 1-(4-cyanobutyl)-3-methyl-2-(3-pyridyl)-indole as an oil.

EXAMPLE 30

A mixture of 578 mg of 1-(4-cyanobutyl)-3-methyl-2-(3-pyridyl)indole, 173 mg of sodium azide, 142 mg of ammonium chloride and 5 mg of lithium chloride in 2 ml of DMF is heated at 120° overnight. After cooling the mixture is filtered and the filtrate diluted with ca. 25 ml of water. After the pH is adjusted to 10–11 with 3 N NaOH, the solution is washed with ether to remove unreacted nitrile. The aqueous phase is adjusted to pH 5–6 with 2 N HCl and extracted with ether. The ether extract is washed with water, dried over MgSO$_4$ and concentrated in vacuo. The solid residue is slurried in petroleum ether and collected to give 1-[4-(5-tetrazolyl)-butyl]-3-methyl-2-(3-pyridyl)indole, m.p. 177°–179°.

EXAMPLE 31

A solution of 3-methyl-2-(3-pyridyl)indole (2.08 g) in 12 ml of DMF is added to a suspension of 0.528 g of 50% sodium hydride (dispersion in mineral oil) in 6 ml of DMF under nitrogen at 10°–15°. After complete addition the mixture is stirred at room temperature for 0.5 hour and is treated with a solution of 2.39 g of ethyl 3-(p-chloromethylphenyl)-2-methylacrylate in 5 ml of DMF dropwise. The resulting mixture is stirred at room temperature overnight and poured in 100 ml of water. The resulting mixture is extracted with ethyl acetate (2×50 ml) and the organic layer is washed with 100 ml of brine, dried over magnesium sulfate and evaporated to yield 1-[p-(2-ethoxycarbonylpropen-1-yl)benzyl]-3-methyl-2-(3-pyridyl)indole.

Hydrolysis with 2N aqueous HCl yields 1-[p-(2-carboxypropen-1-yl)benzyl]-3-methyl-2-(3-pyridyl)indole.

The starting material is prepared as follows:

To a suspension of 10.0 g of 50% sodium hydride (dispersion in mineral oil) in freshly distilled dimethoxyethane (DME, 350 ml) stirred under nitrogen at 10° is added 53.6 ml of triethyl 2-phosphonopropionate in ca. 40 minutes. The mixture is stirred for 0.5 hour at 10° and for an additional 1.5 hours during which time the temperature is allowed to rise to room temperature. This solution is transferred under nitrogen by cannula to a 500 ml addition funnel and is added dropwise to a solution of terephthalaldehyde (33.53 g) in dry DME (475 ml) over a period of 1 hour at 22°–34°. After addition is complete the reaction mixture is stirred mechanically at room temperature for 2 hours, poured into 1L of water and extracted with 4×500 ml of ether. The ether extract is washed with a saturated sodium chloride solution (700 ml), dried over magnesium sulfate, filtered, and concentrated in vacuo to give a yellow oil which partially crystallizes on standing. This crude mixture is purified by suspending in petroleum ether and ethyl acetate (93:7). The filtrate, after removal of unreacted dialdehyde, is concentrated in vacuo to give a mixture which is further purified by high pressure liquid chromatography (using petroleum ether/ethyl acetate 93:7). There is obtained pure ethyl 4-formyl-α-methylcinnamate. A solution of the aldehyde (34.80 g) in 820 ml of absolute ethanol is treated with 12.11 g of granular sodium borohydride at room temperature under nitrogen. The resulting mixture is stirred at room temperature for 3 hours (or until all borohydride has dissolved) and then concentrated to ca. 200 ml volume, diluted with 400 ml of water, and extracted with 3×200 ml of ether. The ether extract is washed with 100 ml of water and brine (100 ml), is dried over magnesium sulfate, filtered, and the filtrate concentrated in vacuo to give ethyl 3 (p-hydroxymethylphenyl)-2-methylacrylate. To a solution of this product in 350 ml of methylene chloride is added at room temperature 11.53 ml of thionyl chloride dropwise over 25 minutes. The clear, colorless solution is stirred for 2 hours. The solution is washed with 100 ml of water, 200 ml of saturated sodium bicarbonate, 100 ml of water, and 100 ml of brine. The organic layer after drying and removal of solvent yields ethyl 3-(p-chloromethylphenyl)-2-methylacrylate, used without further purification.

EXAMPLE 32

1-(5-Formylpentyl)-3-methyl-2-(3-pyridyl)indole (127 mg) is dissolved in DMF (0.66 ml) and pyridinium dichromate (298 mg) added all at once. The mixture is stirred overnight at room temperature then diluted with ether:ethyl acetate (25 ml, 4:1) and filtered. The solid is washed with hot chloroform and the combined filtrates concentrated in vacuo to yield a dark brown gum which is slurried in ether:ethyl acetate (4:1) and extracted with 0.1 N aqueous sodium hydroxide (2 ml). The aqueous extract is acidified to pH 5.5–6.0 and extracted with chloroform. The chloroform extract is dried and concentrated in vacuo yielding a yellow oil; TLC (silica gel, EtOAc:hexane 1:1) indicates the presence of the desired acid. Further purification by chromatography on silica gel using ethyl acetate:hexane (1:1) as the eluent yields the desired 1-(5-carboxypentyl)-2-(3-pyridyl)-3-methylindole of Example 3.

EXAMPLE 33

Bromine (0.344 ml) is added to a solution of 692 mg of sodium hydroxide in 4 ml of water with ice bath cooling. The resulting solution is added to 400 mg of 1-(5-oxohexyl)-3-methyl-2-(3-pyridyl)indole and this mixture is stirred for 2 hours at room temperature. The mixture is washed with ether. The aqueous solution is filtered and acidified to pH 5–6 with 2 N HCl. A crude white solid is collected which melts in the range 108°–120°. TLC (silica gel; methylene chloride/methanol 9:1) separation gives 1-(4-carboxybutyl)-3-methyl-2-(3-pyridyl)indole of Example 5.

The starting material is prepared as follows:

1-(4-cyanobutyl)-3-methyl-2-(3-pyridyl)indole (1.5 g) in 15 ml of ether is added to a solution of 0.0103 mole of methyl magnesium bromide in 15 ml of ether, and this mixture is heated at reflux temperature for 3 hours. After cooling, 10 ml of 6N HCl is added dropwise and this mixture refluxed for several hours. The reaction mixture is washed with ether, and basified to pH 10–11 with 3N NaOH. Ether extraction and evaporation of the solvent yields 1-(5-oxohexyl)-3-methyl-2-(3-pyridyl)- indole; IR 1720 cm$^{-1}$; NMR (CDCl$_3$)δ2.0.

EXAMPLE 34

1-(7-carboxyheptyl)-5-chloro-3-methyl-2-(3-pyridyl)indole hydrochloride (421 mg) dissolved in 7 ml of tetrahydrofuran is warmed and treated with 202 mg (0.278 ml) of triethylamine. This solution is added dropwise to a solution of 108 mg (0.096 ml) of ethyl chloroformate in 1 ml of tetrahydrofuran which is cooled to 0°–5°. The reaction mixture is stirred 1 hour at this temperature and filtered to remove triethylamine hydrochloride. The filtrate is treated with a solution of hydroxylamine hydrochloride (69 mg) and sodium hydroxide (40 mg) in 10 ml of methanol. This mixture is stirred 0.5 hr and concentrated in vacuo. The residue is treated with 25 ml of ether-methanol (10:1) and filtered. The filtrate is evaporated in vacuo leaving a thick oil which is dissolved in acetone and treated with 6.5N ethanolic HCl to give 1-(7-hydroxycarbamoylheptyl)-5-chloro-3-methyl-2-(3-pyridyl)-indole hydrochloride, m.p. 170°–173°.

EXAMPLE 35

Ethanolic hydrogen chloride (7.1 N, 0.14 ml) is added to 236 mg of N-phenyl-N-(5-methoxycarbonylpentyl)-hydrazine in 2 ml of absolute ethanol followed by 135 mg of 3-propionylpyridine. The mixture is heated at reflux temperature overnight. Additional ethanolic HCl (0.62 ml) is added and heating is continued for an additional 24 hours. After cooling, the mixture is filtered and the filtrate evaporated in vacuo. The residue is stirred in 10 ml of water and basified to pH 10–11 with 1 N sodium hydroxide; this mixture is extracted with ether. The extract after washing with water and drying over magnesium sulfate gives on evaporation of solvent an oil which is identified as 1-(5-ethoxycarbonylpentyl)-3-methyl-2-(3-pyridyl)-indole.

This ester is hydrolyzed with 10 ml of 2 N HCl at reflux temperature followed by adjustment of the pH to ca. 6 with saturated sodium bicarbonate and extraction with ether. Workup of the organic extract gives 1-(5-carboxypentyl)-3-methyl-2-(3-pyridyl)indole of Example 3 (crude m.p. 111°–113°).

The starting material is prepared as follows:

Aniline (2.79 g, 2.73 ml), 6.27 g of methyl 6-bromohexanoate and 12.24 g (0.09 mole) of sodium acetate trihydrate are heated at 80°–100° overnight in 15 ml of absolute ethanol. After cooling, the mixture is poured into 75 ml of ice-water and extracted with ether. The organic extract is washed with water, dried over magnesium sulfate and evaporated in vacuo to give N-(5-methoxycarbonylpentyl)aniline.

A solution of 1.4 g of sodium nitrite in 5 ml of water is added dropwise at 0°–10° to a mixture of 4.42 g of N-(5-methoxycarbonylpentyl)-aniline, 2.9 ml of concentrated hydrochloric acid, and ice as needed to maintain the desired temperature. The mixture is then allowed to stir at ambient temperature for 1 hour and is then extracted with ether. The extract is washed with water, dried over magnesium sulfate, and evaporated in vacuo to give N-nitroso-N-(5-methoxycarbonylpentyl)-aniline as an oil.

The above N-nitroso derivative (3.6 g) in 4 ml of glacial acetic acid is added dropwise to 3.94 g of zinc powder in 6 ml of water. After an exothermic reaction to 35°, the mixture is stirred at room temperature for 2 hours. After filtration to remove zinc, the filtrate is washed with ether and basified to pH 10–11 with 40% sodium hydroxide and extracted with ether. The extract is dried over magnesium sulfate and evaporated in vacuo to give a crude oil. After flash chomatography through silica gel with hexane-acetic acid (5:1), N-phenyl-N-(5-methoxycarbonylpentyl)-hydrazine of about 80% purity is obtained, which is used directly in the Fischer cyclization described above.

EXAMPLE 36

1-[7,7-(bis-methoxycarbonyl)heptyl]-3-methyl-2-(3-pyridyl)indole (273 mg) is dissolved in methanol (0.5 ml) and 1 N aqueous lithium hydroxide (1.95 ml) added. The mixture is stirred at room temperature for 1 hour, then refluxed for 2.5 hours. The clear solution is concentrated to dryness, and the residue dissolved in water and the pH adjusted to 6–6.2. A yellow gummy solid precipitates which is extracted into chloroform. Concentration of the chloroform, which is dried over anhydrous magnesium sulfate, yields crude 1-[7,7-(bis-carboxy)heptyl]-3-methyl-2-(3-pyridyl)indole; NMR(CDCl$_3$) δ10.60(2H).

A sample of the crude dicarboxylic acid (28 mg) is heated with p-xylene (3 ml) containing 0.1 N HCl (0.1 ml) for 0.5 hour. The clear solution is allowed to cool to room temperature. A gum precipitates and is extracted into aqueous sodium hydroxide. The aqueous phase is separated, and after adjustment of the pH to 6–6.2, extracted with ethyl acetate:ether (8:2). The organic phase is dried over anhydrous magnesium sulfate and concentrated to give a colorless oil which solidifies on standing to yield 1-(7-carboxyheptyl)-3-methyl-2-(3-pyridyl)-indole, identical by NMR and TLC to the compound of Example 1.

The starting material is prepared as follows:

Thionyl chloride (0.36 ml) is combined with 1-(6-hydroxyhexyl)-3-methyl-2-(3-pyridyl)indole (1.37 g) at 0°. The mixture is then stirred at room temperature for 1 hour. Saturated aqueous sodium bicarbonate is added and the mixture is extracted with dichloromethane. The extract is washed with brine and dried over anhydrous magnesium sulfate. Concentration in vacuo yields the crude chloride as an oil. Purification by silica gel chromatography (CH$_2$Cl$_2$/EtOAc 9.5:0.5) gives 1-(6-chlorohexyl)-3-methyl-2-(3-pyridyl)indole as a light yellow oil; NMR (CDCl$_3$) δ3.30 (t, 2H), 3.92 (t, 2H).

The 1-(6-chlorohexyl)-3-methyl-2-(3-pyridyl)indole (0.5 g) is combined with dimethyl malonate (792 mg), potassium carbonate (790 mg) and dimethylformamide (11.6 ml) and the mixture is heated at 80°–90° for 18 hours under nitrogen. The mixture is poured into ice water (80 ml), and acidified with 1N HCl and washed with ether. The aqueous layer is adjusted to pH 6 and extracted with ether which is then dried over anhydrous magnesium sulfate and concentrated to yield a yellow oil. Purification by preparative TLC (silica gel, CHCl$_3$/EtOAc 9:1) gives 1-[7,7-(bis-methoxycarbonyl)-heptyl]-3-methyl-2-(3-pyridyl)indole; NMR (CDCl$_3$) δ3.32 (t, 1H), 3.78 (s, 6H), 4.03 (t, 2H): IR (neat) 1750 cm$^{-1}$.

EXAMPLE 37

1-(6-Chlorohexyl)-3-methyl-2-(3-pyridyl)indole (165 mg) in dry THF (2 ml) is added dropwise to magnesium turnings (12 mg) in dry THF (2 ml) under a nitrogen atmosphere. A crystal of iodine is added during the addition to initiate the reaction. The mixture is refluxed for 4 hours after the addition is completed, then cooled to 0°, and dry carbon dioxide gas bubbled into the flask with stirring for 15 minutes. The cloudy mixture is poured into 5 ml of 1 N NaOH and extracted with ether. The aqueous phase is adjusted to pH 6–6.2 and extracted with ethyl acetate. The organic phase is dried over anhydrous magnesium sulfate and concentrated in vacuo yielding a white solid, crude mp 106°–107°, being 1-(6-carboxyhexyl)-3-methyl-2-(3-pyridyl)-indole, identical by TLC and NMR to the compound of Example 4.

EXAMPLE 38

1-(Prop-2-ynyl)-3-methyl-2-(3-pyridyl)-indole (90 mg) is dissolved in THF (2 ml) under a nitrogen atmosphere and the resulting solution cooled to −78°. A solution of n-butyl lithium (0.024 ml, 1.6 M in hexane) is added dropwise via syringe over 1 minute. After stirring at −78° for an additional 10 minutes the orange colored mixture is quenched with methyl chloroformate (0.031 ml) and allowed to warm to room temperature. The mixture is then poured into brine and extracted with ether. The ether extract is washed with water and dried over anhydrous magnesium sulfate. Concentration in vacuo yields an oil which is purified by preparative TLC using (1:1) ethyl acetate:hexane as the developing solvent. The 1-(3-methoxycarbonyl-prop-2-ynyl)-3-methyl-2-(3-pyridyl)indole is isolated as an oil; NMR (CDCl$_3$) δ3.73 (s, 3H), 4.83 (s, 2H); IR (CHCl$_3$)1715, 2245 cm$^{-1}$.

The starting material is prepared as follows:

Sodium hydride (50% mineral oil dispersion, 53 mg) is washed with petroleum ether under nitrogen. The washed sodium hydride is suspended in dry DMF (2 ml) and 3-methyl-2-(3-pyridyl)indole (208 mg) in DMF (2 ml) added dropwise. The mixture is stirred an additional 30 minutes followed by the dropwise addition of propargyl bromide (220 mg). The mixture is stirred for an additional 2 hours, poured into ice water, acidified with 1 N HCl and extracted with ether. The aqueous phase is made basic with sodium bicarbonate and extracted with ether. The ether extract is washed with water, brine, and dried over anhydrous magnesium sulfate. Concentration in vacuo yields 1-(prop-2-ynyl)-3-methyl-2-(3-pyridyl)-indole; NMR (CDCl$_3$) δ2.20 (s, 4 H), 4.70 (d, 2 H, J=3 Hz); IR (neat) 3200, 2120 cm$^{-1}$; m.p. 104°–105° after purification with silica gel flash chromatography using ethyl acetate:hexane (1:1).

EXAMPLE 39

Treatment of 33 mg of 1-(3-methoxycarbonylprop-2-ynyl)-3-methyl-2-(3-pyridyl)indole in 1 ml of methanol with 0.3 ml of aqueous 1 N lithium hydroxide at room temperature yields 1-(3-carboxyprop-2-ynyl)-3-methyl-2-(3-pyridyl)indole; IR 1720 cm$^1$.

EXAMPLE 40

Preparation by methods analogous to those described in the previous examples of additional compounds of formula II wherein R$_1'$=CH$_3$, Pyr=3-pyridyl and R$_4$=OH.

| Compound | R$_2'$ | R$_3'$ | CmH$_2$m | Salt | m.p. |
|---|---|---|---|---|---|
| 40/1 | 5-Cl | H | (CH$_2$)$_7$ | HCl | 173–176° |
| 40/2 | 5-OCH$_3$ | H | (CH$_2$)$_5$ | HBr | 188–189° |
| 40/3 | 5-Cl | 6-Cl | (CH$_2$)$_5$ | HCl | 178–80° |
| 40/4 | 5-F | H | (CH$_2$)$_5$ | HCl | 216–219° |
| 40/5 | 5-CH$_3$ | H | (CH$_2$)$_5$ | HCl | 185–8° |
| 40/6 | 5-CH$_3$ | H | (CH$_2$)$_7$ | — | 124–125° |
| 40/7 | H | H | (CH$_2$)$_{10}$ | — | 100–102° |
| 40/8 | 5-O—CH$_2$—O-6 | | (CH$_2$)$_5$ | — | |
| 40/9 | 5-OH | H | (CH$_2$)$_5$ | — | 168–170° |
| 40/10 | 5-SCH$_3$ | H | (CH$_2$)$_5$ | — | 135–7° |
| 40/11 | H | H | (CH$_2$)$_{11}$ | — | 99–101° |
| 40/12 | H | H | (CH$_2$)$_9$ | — | 106–108° |

The starting N-unsubstituted indoles are known in the literature; the starting material for compound 40/10, 5-methylthio-2-(3-pyridyl)-3-methylindole, has m.p. of 160°–162°.

The compound of example 40/9 is prepared by hydrogenolysis of 1-(5-carboxypentyl)-5-benzyloxy-2-(3-pyridyl)-3-methylindole, m.p. 176°–178°. The starting 5-benzyloxy-2-(3-pyridyl)-3-methylindole has m.p. 164°–166°.

EXAMPLE 41

Preparation by methods analogous to those described in the previous examples of additional compounds of formula I wherein R$_1$=CH$_3$, Ar=3-pyridyl, and B=COOH

| Example | R$_2$ | R$_3$ | A |
|---|---|---|---|
| 41/1 | H | H | C≡C—(CH$_2$)$_3$ |
| 41/2 | H | H | CH$_2$S(CH$_2$)$_2$ |
| 41/3 | H | H | (CH$_2$)$_2$—O—(CH$_2$)$_2$ |
| 41/4 | H | H | (CH$_2$)$_2$—O—(CH$_2$)$_3$ |

The alkylating starting materials for compounds of examples 41/2 and 41/3, 41/4 are prepared as described in J. Org. Chem. 34, 2955 (1969), U.S. Pat. No. 3,984,459 and Chem Abstr. 83, 166177b respectively.

EXAMPLE 42

1-(5-carboxypentyl-3-carboxy-5-hydroxy-2-(3-pyridyl)indole is heated at the melting point in an oil bath under nitrogen to yield 1-(5-carboxypentyl)-5-hydroxy-2-(3-pyridyl)indole.

The starting material is prepared as follows:

A mixture of 196 mg of ethyl nicotinoylacetate and 192 mg of ethyl 6-aminocaproate is heated at 120°–130° under nitrogen for 18 hours. The product is purified by preparative TLC (silica gel; chloroform, ethyl acetate 9.1) to yield ethyl β-(3-pyridyl)-β-(5-ethoxycarbonylpentylamino)acrylate;R$_f$=0.3.

A solution of 0.334 g of ethyl β-(3-pyridyl)-β-(5-ethoxycarbonylpentylamino)acrylate and 0.108 g of p-benzoquinone in 1 ml of glacial acetic (according to the general procedure as described in J. Chem. Soc. C 1968, 1795) is heated at 60° for 4 hours. The reaction mixture is cooled, diluted with 10 ml of water, neutralized to pH 7 with saturated sodium bicarbonate solution and extracted with methylene chloride. The methylene chloride extract is dried, evaporated to dryness and the resulting product is purified by preparative TLC (silica gel; ethyl acetate, hexane 1:1) to give 1-(5-ethoxycarbonylpentyl-3-ethoxycarbonyl-5-hydroxy-2-(3-pyridyl)indole, NMR δ3.95, 4.1, 8.75.

Hydrolysis with 10% potassium hydroxide yields after customary workup 1-(5-carboxypentyl)-3-carboxy-5-hydroxy-2-(3-pyridyl)indole.

What is claimed is:

1. A compound of the formula

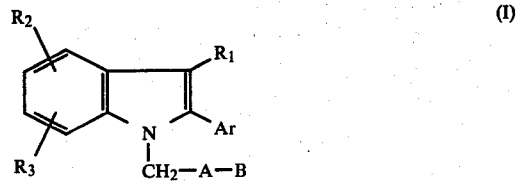

(I)

wherein

R$_1$ represents hydrogen or lower alkyl;

Ar represents pyridyl unsubstituted or substituted by lower alkyl, carboxy, lower alkoxycarbonyl or carbamoyl;

R$_2$ and R$_3$ independently represent hydrogen, lower alkyl, halogen, trifluoromethyl, hydroxy, lower alkoxy, carboxy lower alkyl, lower alkoxycarbonyl lower alkyl, carboxy, lower alkoxycarbonyl, or lower alkyl-(thio, sulfinyl or sulfonyl), or R₂ and R₃ together on adjacent carbon atoms represent lower alkylenedioxy;

A represents straight chain or branched alkylene of 1 to 12 carbon atoms, alkenylene of 2 to 12 carbon atoms, alkynylene of 2 to 12 carbon atoms, lower alkylenephenylene lower alkylene, lower alkylenephenylene, phenylene lower alkylene, phenylene, a direct bond, lower alkylene-(thio or oxy)-lower alkylene, (thio-or oxy)-phenylene, lower alkylene-(thio or oxy)-phenylene, phenylene-(thio or oxy)-lower alkylene or phenylene lower alkenylene;

B represents carboxy, lower alkoxycarbonyl, carbamoyl, mono-or di-lower alkylcarbonoyl, formyl, 5-tetrazolyl or hydroxycarbamoyl; or a pharmaceutically acceptable salt thereof.

2. A compound of the formula

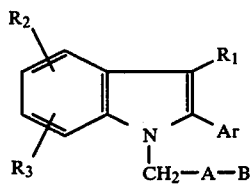

(I)

wherein
R₁ represents hydrogen or lower alkyl; Ar represents 2-, 3- or 4-pyridyl or 2-, 3- or 4-pyridyl substituted by lower alkyl;
R₂ is hydrogen, lower alkyl, halogen, trifluoromethyl, hydroxy, lower alkoxy, lower alkylthio, carboxy lower alkyl or lower alkoxycarbonyl lower alkyl;
R₃ is hydrogen; or R₂ and R₃ together on adjacent carbon atoms represent lower alkylenedioxy;
A represents straight chain or branched alkylene of 3 to 10 carbon atoms, phenylene, lower alkylenethio-phenylene or lower alkylene-oxy-phenylene of 7 to 10 carbon atoms each;
B represents carboxy, lower alkoxycarbonyl, carbamoyl, hydroxycarbamoyl, 5-tetrazolyl, or hydroxymethyl; or a pharmaceutically acceptable salt thereof.

3. A compound of claim 1 wherein B represents carboxy, lower alkoxycarbonyl, carbamoyl, 5-tetrazolyl or hydroxy carbamoyl; or a pharmaceutically acceptable salt thereof.

4. A compond of claim 1 wherein A represents straight chain or branched alkylene of 1 to 12 carbon atoms, phenylene or a direct bond; or a pharmaceutically acceptable salt thereof.

5. A compound of claim 1 of the formula

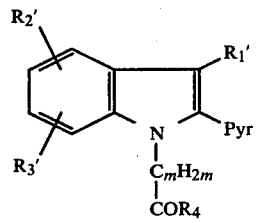

(II)

wherein
R₁' represents hydrogen or lower alkyl;
R₂' and R₃' represent independently hydrogen, lower alkyl, halogen, trifluoromethyl, hydroxy, lower alkylthio or lower alkoxy; or R₂' and R₃' together on adjacent carbon atoms represent methylenedioxy;
Pyr represents 2-, 3- or 4-pyridyl;
m represents an integer from 1 to 13;
R₄ represents hydroxy, lower alkoxy or amino; or a pharmaceutically acceptable salt thereof.

6. A compound of claim 5 wherein
R₁' represents hydrogen or lower alkyl;
R₂' represehts hydrogen, lower alkyl, halogen, trifluoromethyl, hydroxy, lower alkylthio or lower alkoxy;
R₃' represents hydrogen;
Pyr represents 2-, 3- or 4-pyridyl;
m represents an integer from 1 to 13;
R₄ represents hydroxy, lower alkoxy or amino; or a pharmaceutically acceptable salt thereof.

7. A compound of claim 5 wherein
R₁' represents methyl, ethyl, propyl;
R₂' represents hydrogen, methyl, chloro, fluoro, trifluoromethyl, hydroxy, methylthio or methoxy;
m represents an integer from 3 to 10;
R₄ represents hydroxy, ethoxy, methoxy or amino;
Pyr represents 3- or 4-pyridyl; or a pharmaceutically acceptable salt thereof.

8. A compound of claim 1 of the formula

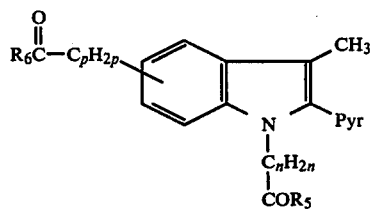

(III)

wherein
n represents an integer from 3 to 10;
p represents an integer from 0 to 4;
Pyr represents 2-, 3- or 4-pyridyl;
R₅ and R₆ independently represent hydroxy or lower alkoxy; or a pharmaceutically acceptable salt thereof.

9. A compound of claim 1 of the formula

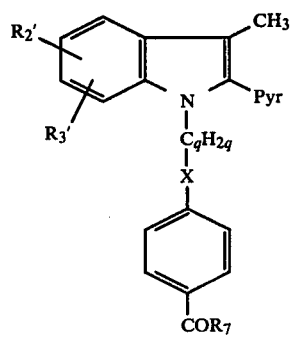

(IV)

wherein R₂' and R₃' independently represent hydrogen, lower alkyl, halogen, lower alkoxy, lower alkylthio or hydroxy; or R₂' and R₃' together on adjacent carbon atoms represent methylenedioxy; X represents oxygen, sulfur or a direct bond; q represents an integer from 1 to 4; R₇ represents hydroxy or lower alkoxy; Pyr represents 2-, 3- or 4-pyridyl, or a pharmaceutically acceptable salt thereof.

10. A compound of claim 9 wherein X represents a direct bond; or a pharmaceutically acceptable salt thereof.

11. A compound of claim 9 wherein X represents oxygen or sulfur; 8 is an integer from 2 to 4; or a pharmaceutically acceptable salt thereof.

12. A compound of claim 1 being 1-(7-carboxyheptyl)-3-methyl-2-(3-pyridyl)-indole or a pharmaceutically acceptable acid addition, metal or ammonium salt thereof.

13. A compound of claim 1 being 1-(4-carboxybutyl)-3-methyl-2-(3-pyridyl)-indole or a pharmaceutically acceptable acid addition, metal or ammonium salt thereof.

14. A compound of claim 1 being 1-(5-carboxypentyl)-5-chloro-3-methyl-2-(3-pyridyl)-indole or a pharmaceutically acceptable acid addition, metal or ammonium salt thereof.

15. A compound of claim 1 being 1-(5-carboxypentyl)-3-methyl-5-(2-carboxyethyl)-2-(3-pyridyl)-indole; 1-[2-(4-carboxyphenylthio)ethyl]-2-(3-pyridyl)-3-methylindole; 1-[2-(4-carboxyphenoxy)ethyl]-2-(3-pyridyl)-3-methylindole; 1-(4-carboxybenzyl)-3-methyl-2-(3-pyridyl)-indole; or a pharmaceutically acceptable acid addition, metal or ammonium salt thereof.

16. A pharmaceutical composition suitable for oral or parenteral administration to mammals for the treatment of diseases responsive to inhibition of thromboxane synthetase comprising an effective amount of a compound of claim 1 in combination with one or more pharmaceutically acceptable carriers.

17. A composition of claim 16 wherein the compound is 1-(7-carboxyheptyl)-3-methyl-2-(3-pyridyl)indole, 1-(5-carboxypentyl)-5-chloro-3-methyl-2-(3-pyridyl)indole or a pharmaceutically acceptable acid addition, metal or ammonium salt thereof.

18. A pharmaceutical composition suitable for oral or parenteral administration to mammals for treatment of diseases responsive to inhibition of thromboxane synthetase comprising an effective amount of a compound of claim 2 in combination with one or more pharmaceutically acceptable carriers.

19. A method of selectively inhibiting the synthesis of thromboxane in a mammal comprising the administration to said mammal of an effective amount of a compound of the formula

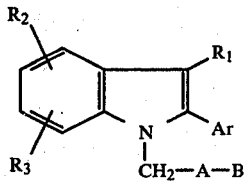

wherein
$R_1$ represents hydrogen or lower alkyl;
Ar represents pyridyl unsubstituted or substituted by lower alkyl, carboxy, lower alkoxycarbonyl or carbamoyl;
$R_2$ and $R_3$ independently represent hydrogen, lower alkyl, halogen, trifluoromethyl, hydroxy, lower alkoxy, carboxy lower alkyl, lower alkoxycarbonyl lower alkyl, carboxy, lower alkoxycarbonyl, or lower alkyl-(thio, sulfinyl or sulfonyl); or $R_2$ and $R_3$ together on adjacent carbon atoms represent lower alkylenedioxy;
A represents straight chain or branched alkylene of 1 to 12 carbon atoms, alkenylene of 2 to 12 carbon atoms, alkynylene of 2 to 12 carbon atoms, lower alkylenephenylene lower alkylene, lower alkylenephenylene, phenylene lower alkylene, phenylene, a direct bond, lower alkylene-(thio or oxy)-lower alkylene, (thio-or oxy)-phenylene, lower alkylene-(thio or oxy)-phenylene, phenylene-(thio or oxy)-lower alkylene or phenylene lower alkenylene;
B represents carboxy, lower alkoxycarbonyl, carbamoyl, mono- or di-lower alkylcarbamoyl, hydroxymethyl, hydroxycarbamoyl, 5-tetrazolyl or formyl; the N-oxide thereof; or a pharmaceutically acceptable salt thereof; in combination with one or more pharmaceutically acceptable carriers.

20. A method of treating diseases responsive to thromboxane synthetase inhibition in mammals comprising the administration to a mammal in need thereof of a therapeutically effective amount of a compound of the formula

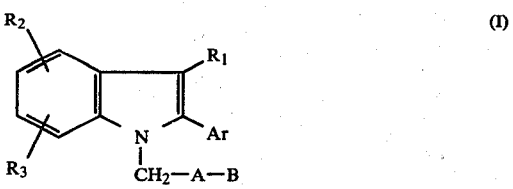

wherein
$R_1$ represents hydrogen or lower alkyl;
Ar represents pyridyl unsubstituted or substituted by lower alkyl, carboxy, lower alkoxycarbonyl or carbamoyl;
$R_2$ and $R_3$ independently represent hydrogen, lower alkyl, halogen, trifluoromethyl, hydroxy, lower alkoxy, carboxy lower alkyl, lower alkoxycarbonyl lower alkyl, carboxy, lower alkoxycarbonyl, or lower alkyl-(thio, sulfinyl or sulfonyl); or $R_2$ and $R_3$ together on adjacent carbon atoms represent lower alkylenedioxy;
A represents straight chain or branched alkylene of 1 to 12 carbon atoms, alkenylene of 2 to 12 carbon atoms, alkynylene of 2 to 12 carbon atoms, lower alkylenephenylene lower alkylene, lower alkylenephenylene, phenylene lower alkylene, phenylene, a direct bond, lower alkylene-(thio or oxy)-lower alkylene, (thio-or oxy)-phenylene, lower alkylene-(thio or oxy)-phenylene, phenylene-(thio or oxy)-lower alkylene or phenylene lower alkenylene;
B represents carboxy, lower alkoxycarbonyl, carbamoyl, mono- or di-lower alkylcarbamoyl, hydroxymethyl, hydroxycarbamoyl, 5-tetrazolyl or formyl; the N-oxide thereof; or a pharmaceutically acceptable salt thereof; in combination with one or more pharmaceutically acceptable carriers.

21. A method according to claim 19 comprising the administration of a therapeuticaly effective amount of 1-(7-carboxy-heptyl)-3-methyl-2-(3-pyridyl)indole, 1-(5-carboxypentyl)-5-chloro-3-methyl-2-(3-pyridyl)-indole, or a pharmaceutically acceptable acid addition, metal or ammonium salt thereof.

22. A method according to claim 20 comprising the administration of a effective amount of 1-(7-carboxyheptyl)-3-methyl-2-(3-pyridyl)indole, 1-(5-carboxypentyl)-5-chloro-3-methyl-2-(3-pyridyl)indole; or a pharmaceutically acceptable acid addition, metal or ammonium salt thereof.

* * * * *

UNITED STATES PATENT AND TRADEMARK OFFICE
CERTIFICATE OF CORRECTION

PATENT NO. : 4,478,842

DATED : October 23, 1984

INVENTOR(S) : Harris B. Renfroe

It is certified that error appears in the above-identified patent and that said Letters Patent is hereby corrected as shown below:

Claim 1, Column 35, Line 14 should read-- oyl, mono-or di-lower alkylcarbomoyl, formyl, --.

Signed and Sealed this

Twenty-fourth Day of September 1985

[SEAL]

Attest:

DONALD J. QUIGG

Attesting Officer

Commissioner of Patents and Trademarks—Designate